United States Patent [19]

Ohkawa et al.

[11] Patent Number: 6,011,046
[45] Date of Patent: Jan. 4, 2000

[54] QUINONE COMPOUND, ITS PRODUCTION AND USE AS ANTIOXIDANT

[75] Inventors: Shigenori Ohkawa, Takatsuki; Yasuo Nagai, Minoo, both of Japan

[73] Assignee: Takeda Chemical Industries, Ltd., Osaka, Japan

[21] Appl. No.: 08/727,599

[22] PCT Filed: Aug. 19, 1996

[86] PCT No.: PCT/JP96/02313

§ 371 Date: Oct. 26, 1996

§ 102(e) Date: Oct. 26, 1996

[87] PCT Pub. No.: WO97/07109

PCT Pub. Date: Feb. 27, 1997

[30] Foreign Application Priority Data

Aug. 21, 1995 [JP] Japan ................................ 7-211629

[51] Int. Cl.⁷ ...................... C07D 211/34; A61K 31/445
[52] U.S. Cl. .................. 514/317; 514/319; 514/320; 546/192; 546/196; 546/236; 546/239
[58] Field of Search .................... 546/236, 239, 546/196, 192; 514/319, 317, 320

[56] References Cited

U.S. PATENT DOCUMENTS 5,059,627 10/1991 Goto et al. .............................. 514/688
5,283,546 2/1994 Regnier et al. ......................... 514/255

FOREIGN PATENT DOCUMENTS 0092136 10/1983 European Pat. Off. .
0533579 3/1993 European Pat. Off. .
0576766 1/1994 European Pat. Off. .
88/08424 11/1988 WIPO .
WO 05192 2/1996 WIPO .

OTHER PUBLICATIONS

Diplock et al. "Vitamine E. Biochemistry and healthe implications"N. Y. Aca. Sci. v. 570, pp. 4–5, 1989.
Verne–Mismer et al. "Evaluation of deactivated reversed phases for the analysis of an . . . "CA 119:176879, 1993.
International dicationary of medicine and biology, Wiley & Sons, vo. 1, pp. 561–562, 1992.

*Primary Examiner*—Ceila Chang
*Attorney, Agent, or Firm*—Fitzpatrick, Cella, Harper & Scinto

[57] ABSTRACT

A compound of the formula (I):

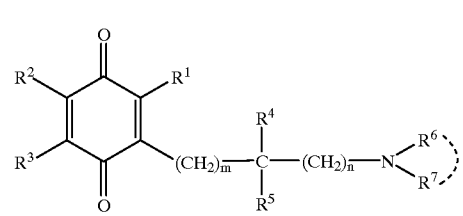

wherein $R^1$, $R^2$ and $R^3$ independently represent H, an optionally acylated hydroxyl group, an optionally substituted amino group, an optionally substituted alkoxy group or an optionally substituted hydrocarbon group, or $R^2$ and $R^3$ may form an optionally substituted hydrocarbon ring; $R^4$ represents an alkyl group; $R^5$ represents an optionally substituted hydroxyl group; $R^6$ and $R^7$ independently represent an optionally substituted hydrocarbon group or $R^6$ and $R^7$ form an optionally substituted ring; m represents 1 or 2; and n represents an integer of 1 to 5; or a hydroquinone derivative or a salt thereof has lipoperoxide formation inhibitory effect and is useful as a medicine for treating or preventing central nervous system disorders, diseases in the circulatory system, etc.

18 Claims, No Drawings

QUINONE COMPOUND, ITS PRODUCTION AND USE AS ANTIOXIDANT

This application is a 371 of PCT/JP96/02313 filed Aug. 19, 1996.

FIELD OF THE INVENTION

The present invention relates to a novel quinone compound, a process for producing it, and a pharmaceutical composition containing it as an active ingredient. The novel quinone compound is useful as an agent for preventing or treating various diseases such as arteriosclerosis, hepatic diseases, cerebrovascular disorders and central nervous damages.

BACKGROUND OF THE INVENTION

As it has become evident that lipoperoxide (peroxylipid) formation in the body and concomitant radical reactions have various harmful effects on the living body through membrane disorders, enzymatic disorders, etc., various attempts to use antioxidants and lipoperoxide formation inhibitors as medicines have been made. At present, the main lipoperoxide formation inhibitors used in the field of medicine are derivatives of natural antioxidants such as vitamin C, vitamin E, etc., and phenol derivatives (Kenji Fukuzawa, The Japanese Journal of Clinical Medicine, 46, 2269–2276, 1988). However, these compounds are not necessarily satisfactory for practical use.

It is believed that the entry of sodium ions through sodium channels into cells results in cell death or tissue damage. It is reported that tetrodotoxin, a sodium channel blocker, relieves such damage. However tetrodotoxin cannot be used for therapy because it is highly toxic (Neurosci. Lett., Vol. 121, pp. 251–254 (1991)).

U.S. Pat. No. 5,059,627 discloses a quinone or hydroquinone compound having nerve growth factor secretion inducing activity. However, this literature fails to specifically disclose a quinone or hydroquinone compound containing 2- or 3-(optionally substituted hydroxy)alkyl or (optionally substituted amino)alkyl on the quinone nucleus, or its lipoperoxide formation inhibitory effect.

Free Radical Biology & Medicine, Vol. 19, No. 2, pp. 197–207 (1995) discloses 2-(3-hydroxy-3-methylbutyl)-3,5,6-trimethyl-1,4-benzoquinone or its hydroquinone derivative. However, this literature fails to specifically discloses a quinone or hydroquinone compound containing (optionally substituted amino)alkyl on the quinone nucleus, or its lipoperoxide formation inhibitory effect.

In view of the above, the main object of the present invention is to provide a novel quinone or hydroquinone compound having excellent lipoperoxide formation inhibitory effect and sodium channel blocking effect, an industrially advantageous process for producing it, and a pharmaceutical composition containing it as an active ingredient.

SUMMARY OF THE INVENTION

The present inventors have synthesized many novel compounds and tested their lipoperoxide formation inhibitory effect, binding affinity for sodium channels, etc. As a result, it has been found that a certain kind of novel quinone compound has advantageous pharmaceutical properties such as potent lipoperoxide formation inhibitory effect, high affinity for sodium channels, etc. After further studies based on these findings, the present invention has been accomplished.

The present invention provides (1) a compound of the formula (I):

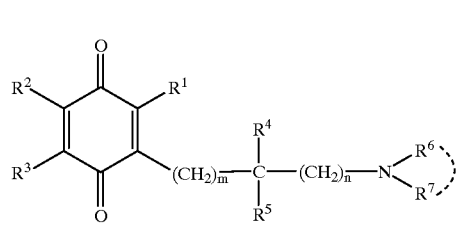

wherein $R^1$, $R^2$ and $R^3$ independently represent hydrogen, an optionally acylated hydroxyl group, an optionally substituted amino group, an optionally substituted alkoxy group or an optionally substituted hydrocarbon group, or $R^2$ and $R^3$, taken together with the adjacent two carbon atoms, may form an optionally substituted hydrocarbon ring;

$R^4$ represents an alkyl group;

$R^5$ represents an optionally substituted hydroxyl group;

$R^6$ and $R^7$ independently represent an optionally substituted hydrocarbon group or $R^6$ and $R^7$, taken together with the adjacent nitrogen atom, form an optionally substituted ring;

m represents 1 or 2; and n represents an integer of 1 to 5; (hereinafter referred to briefly as compound (I)) or its hydroquinone derivative or a salt thereof.

Preferably, the compound of above item (1) is:

(2) a compound of above item (1), wherein $R^2$ and $R^3$ are independently an optionally substituted alkoxy group when $R^6$ and $R^7$ are independently an optionally substituted hydrocarbon group;

(3) a compound of above item (1), wherein $R^6$ and $R^7$, taken together with the adjacent nitrogen atom, form an optionally substituted ring;

(4) a compound of above item (1), wherein $R^1$, $R^2$ and $R^3$ are independently i) hydrogen, ii) a hydroxyl group optionally substituted by a $C_{1-6}$ alkyl-carbonyl, $C_{6-10}$ aryl-carbonyl, $C_{6-10}$ aryl-$C_{1-6}$ alkyl-carbonyl, $C_{1-6}$ alkylsulfonyl, $C_{6-10}$ arylsulfonyl or $C_{6-10}$ aryl-$C_{1-6}$ alkylsulfonyl, iii) an amino group which may be substituted by 1 or 2 substituents selected from the group consisting of
(a) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of a hydroxyl, $C_{1-3}$ alkoxy, $C_{6-10}$ aryl-$C_{1-6}$ alkyloxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of a $C_{1-3}$ alkyl, $C_{6-10}$ aryl-$C_{1-6}$ alkyl, $C_{6-10}$ aryl and 5- to 10-membered heteroaryl, and (b) a 5- to 10-membered heterocyclic group containing, besides carbon atom(s), 1 to 3 hetero atoms selected from nitrogen atom, oxygen atom and sulfur atom, which group may be substituted by 1 to 5 substituents selected from the group consisting of an amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto, iv) a $C_{1-6}$ alkoxy group optionally substituted by 1 to 5 substituents selected from the group consisting of an amino, mono-$C_{1-3}$ alkylamino, di-$C_{1-3}$ alkylamino, halogen, hydroxyl, $C_{1-6}$ alkoxy and $C_{1-6}$ alkylmercapto, or v) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of a hydroxyl, $C_{1-3}$ alkoxy, $C_{6-10}$ aryl-$C_{1-6}$ alkyloxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkynylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of a $C_{1-3}$ alkyl, $C_{6-10}$ aryl-$C_{1-6}$ alkyl, $C_{6-10}$ aryl and 5- to 10-membered heteroaryl, or $R^2$ and $R^3$, taken together with the adjacent two carbon atoms, may form a $C_{6-14}$ aromatic hydrocarbon or $C_{5-8}$ cycloalkene ring which may be substituted by 1 to 3 substituents selected from the group consisting of a $C_{1-3}$ alkyl, $C_{1-3}$ alkoxy, hydroxyl, halogen and amino, $R^4$ is a $C_{1-6}$ alkyl group, $R^5$ is a hydroxyl group optionally substituted by i) a $C_{1-6}$ alkyl, $C_{6-10}$ aryl, $C_{7-10}$ aralkyl, $C_{1-6}$ alkylcarbonyl, $C_{6-10}$ aryl-carbonyl, $C_{7-10}$ aralkylcarbonyl, tetrahydropyranyl or tetrahydrofuranyl group, each of which may be substituted by 1 to 3 substituents selected from the group consisting of a halogen, $C_{1-6}$ alkyl, $C_{6-10}$ aryl, $C_{7-10}$ aralkyl and nitro ii) a formyl or silyl group, each of which may be substituted by 1 to 3 substituents selected from the group consisting of a $C_{1-6}$ alkyl, $C_{6-10}$ aryl and $C_{7-10}$ aralkyl, $R^6$ and $R^7$ are independently a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of a hydroxyl, $C_{1-3}$ alkoxy, $C_{6-10}$ aryl-$C_{1-6}$ alkyloxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of a $C_{1-3}$ alkyl, $C_{6-10}$ aryl-$C_{1-6}$ alkyl, $C_{6-10}$ aryl and 5- to 10-membered heteroaryl, or $R^6$ and $R^7$, taken together with the adjacent nitrogen atom, form a 3- to 7-membered N-containing heterocyclic ring optionally containing, besides carbon atom(s) and a nitrogen atom, 1 to 3 hetero atoms selected from nitrogen atom, oxygen atom and sulfur atom, which ring may be substituted by 1 to 5 substituents selected from the group consisting of an amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto;

(5) a compound of above item (1), wherein $R^1$, $R^2$ and $R^3$ are independently a $C_{1-6}$ alkyl or $C_{1-6}$ alkoxy;

(6) a compound of above item (1), wherein $R^4$ is a $C_{1-6}$ alkyl;

(7) a compound of above item (1), wherein $R^5$ is hydroxyl;

(8) a compound of above item (1), wherein $R^6$ and $R^7$, taken together with the adjacent nitrogen atom, form a 3- to 7-membered saturated N-containing heterocyclic ring optionally containing, besides carbon atom(s) and a nitrogen atom, 1 to 3 hetero atoms selected from nitrogen atom, oxygen atom and sulfur atom, which ring may be substituted by 1 to 5 substituents selected from the group consisting of an amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto;

(9) a compound of above item (1), wherein $R^6$ and $R^7$, taken together with the adjacent nitrogen atom, form a 6-membered N-containing heterocyclic ring optionally containing, besides carbon atom(s) and a nitrogen atom, 1 to 3 hetero atoms selected from nitrogen atom, oxygen atom and sulfur atom, which ring may be substituted by a $C_{6-14}$ aryl;

(10) a compound of above item (1), wherein $R^1$ is a $C_{1-6}$ alkyl, $R^2$ and $R^3$ are independently a $C_{1-6}$ alkyl or $C_{1-6}$ alkoxy, $R^4$ is a $C_{1-6}$ alkyl, $R^5$ is hydroxyl, $R^6$ and $R^7$, taken together with the adjacent nitrogen atom, form a 6-membered N-containing heterocyclic ring optionally containing, besides carbon atom(s) and a nitrogen atom, 1 to 3 hetero atoms selected from nitrogen atom and oxygen atom, which ring may be substituted by a $C_{6-14}$ aryl, m is 1, and n is 1 or 5;

(11) a compound of above item (1), wherein the hydroquinone derivative is a compound of the formula (I'):

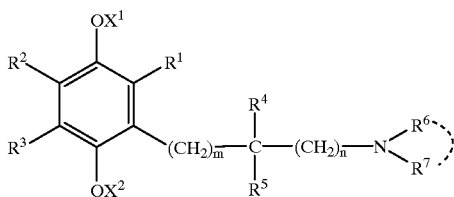

wherein $X^1$ and $X^2$ independently represent hydrogen, an optionally substituted hydrocarbon group, an optionally substituted aromatic group or an acyl group, and the other symbols are as defined in above item (1) (hereinafter referred to briefly as compound (I')), or a salt thereof;

(12) a compound of above item (1), which is 2-[2-hydroxy-2-methyl-3-(4-phenylpiperidin-1-yl)propyl]-3,5,6-trimethyl-1,4-benzoquinone or a salt thereof; or

(13) a compound of above item (1), which is (S)-2-[2-hydroxy-2-methyl-3-(4-phenylpiperidin-1-yl)propyl]-3,5,6-trimethyl-1,4-benzoquinone or a salt thereof.

The present invention also provides (14) a process for producing a compound of above item (1) which comprises subjecting a compound of the formula (II):

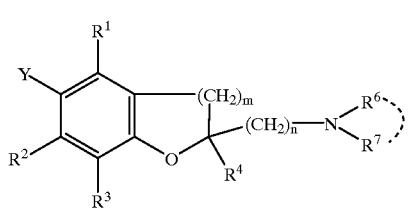

wherein Y represents —$NR^8R^9$ or —$OR^{10}$ wherein $R^8$, $R^9$ and $R^{10}$ independently represent hydrogen, an optionally substituted hydrocarbon group or an acyl group, and the other symbols are as defined in above item (1), or a salt thereof, to oxidation and if necessary subjecting the resultant compound to any one or more of protection, reduction, acylation, alkylation, oxidation, hydrogenation, carbon-chain extension, substitution and deprotection.

The present invention also provides (15) a pharmaceutical composition which comprises a compound of above item (1), if necessary together with a pharmaceutically acceptable carrier.

Preferably, the composition of above item (15) is:

(16) a composition of above item (15) which is for inhibition of lipoperoxide formation;

(17) a composition of above item (15) which is for treating neurological disorders caused by central nervous system damage;

(18) a composition of above item (17), wherein the central nervous system damage is cranial injury or spinal injury;

(19) a composition of above item (15) which is for treating dysmnesia or emotional disturbance;

(20) a composition of above item (19), wherein the dysmnesia or emotional disturbance is accompanied by nerve cell necrosis caused by cerebral lesion, cerebral hemorrhage or cerebral infarction;

(21) a composition of above item (15) which is for improving circulatory system of heart or brain; or

(22) a composition of above item (15) which is for treating cerebral edema.

DETAILED DESCRIPTION OF THE INVENTION

In the above formulas, when the hydroxyl group represented by $R^1$, $R^2$ or $R^3$ is acylated, the acyl groups include, for example, acyl groups derived from organic carboxylic or sulfonic acids. Preferred examples of the acyl groups include a hydroxyl group substituted by a $C_{1-6}$ alkyl-carbonyl (e.g., acetyl, propionyl, butyryl, isobutyryl), $C_{6-10}$ aryl-carbonyl (e.g., benzoyl, naphthoyl), $C_{6-10}$ aryl-$C_{1-6}$ alkyl-carbonyl (e.g., benzylcarbonyl, phenethylcarbonyl, naphthylmethylcarbonyl), $C_{1-6}$ alkylsulfonyl (e.g., mesyl, ethylsulfonyl, propylsulfonyl), $C_{6-10}$ arylsulfonyl (e.g., phenylsulfonyl, naphthylsulfonyl, tosyl) or $C_{6-10}$ aryl-$C_{1-6}$ alkylsulfonyl (e.g., benzylsulfonyl, phenethylsulfonyl, naphthylmethylsulfonyl).

When the optionally substituted amino group represented by $R^1$, $R^2$ or $R^3$ is substituted, examples of the substituents are the optionally substituted hydrocarbon groups represented by $R^1$, $R^2$ or $R^3$ described hereinafter and the optionally substituted aromatic groups, preferably aromatic heterocyclic groups.

The aromatic groups of the optionally substituted aromatic groups include, for example, aromatic hydrocarbon groups, and aromatic heterocyclic groups.

The aromatic hydrocarbon groups include, for example, monocyclic or condensed polycyclic aromatic hydrocarbon groups having 6 to 14 carbon atoms. Examples of the aromatic hydrocarbon groups include $C_{6-14}$ aryl groups such as phenyl, 1-naphthyl, 2-naphthyl, biphenylyl, indenyl and anthryl. Preferred examples thereof are phenyl, 1-naphthyl and 2-naphthyl. In particular, phenyl is preferred.

The aromatic heterocyclic groups include, for example, 5- to 11-membered (preferably 5- to 10-membered) monocyclic groups containing, besides carbon atoms, at least one hetero atom (for example, 1 to 4 hetero atoms) selected from nitrogen, sulfur and oxygen atoms, and their condensed aromatic heterocyclic groups. Examples of the aromatic heterocyclic groups include monovalent groups formed by removing any one hydrogen atom from aromatic heterocyclic rings such as thiophene, benzo[b]thiophene, benzo[b]furan, benzimidazole, benzoxazole, benzothiazole, furan, pyrrole, imidazole, pyrazole, pyridine, pyrazine, pyrimidine, pyridazine, indole, 1H-indazole, isoquinoline and quinoline, or condensed rings formed by these heterocyclic rings and one or more (preferably one or two) aromatic rings (e.g., benzene ring).

The substituents of the optionally substituted aromatic groups include, for example, amino, mono- or di-alkylamino groups (the alkyl of which being lower alkyl having 1 to 3 carbon atoms such as methyl, ethyl and propyl), halogen (e.g., fluorine, chlorine, bromine, iodine), nitro, sulfo, cyano, hydroxyl, carboxyl, lower alkyl groups having 1 to 5 carbon atoms (e.g., methyl, ethyl, propyl, butyl), aryl groups having 6 to 14 carbon atoms (e.g., phenyl, naphthyl, indenyl, anthryl), lower alkoxy groups having 1 to 3 carbon atoms (e.g., methoxy, ethoxy, propoxy), acyl groups having 2 to 5 carbon atoms (e.g., $C_{1-4}$ alkyl-carbonyl such as acetyl, propionyl and butyryl), and lower alkylmercapto groups having 1 to 3 carbon atoms (e.g., methylmercapto, ethylmercapto). The number of the substituent(s) is not specifically limited, and it is 1 to 5, preferably 1 to 3. When the number of the substituent is two or more, each substituent may be the same as or different from one another.

The alkoxy groups of the optionally substituted alkoxy groups represented by $R^1$, $R^2$ or $R^3$ include, for example, alkoxy groups (e.g., $C_{1-6}$ alkoxy groups) containing straight-chain or branched $C_{1-6}$ alkyl groups or $C_{3-6}$ cycloalkyl groups. The substituents which the alkoxy groups may have include, for example, amino, mono- or di-alkylamino groups (the alkyl of which being lower alkyl having 1 to 3 carbon atoms such as methyl, ethyl, propyl), halogen (e.g., fluorine, chlorine, bromine, iodine), hydroxyl, lower alkoxy groups having 1 to 6 carbon atoms (e.g., methoxy, ethoxy, propoxy, butoxy), and lower alkylmercapto groups having 1 to 6 carbon atoms (e.g., methylmercapto, ethylmercapto, propylmercapto). The number of the substituent(s) is 1 to 5, preferably 1 to 3. When the number of the substituent is two or more, each substituent may be the same as or different from one another.

The hydrocarbon groups of the optionally substituted hydrocarbon groups represented by $R^1$, $R^2$ or $R^3$ may be saturated or unsaturated. Examples of the hydrocarbon groups include alkyl groups, alkenyl groups, alkynyl groups, cycloalkyl groups, aryl groups and aralkyl groups. In particular, hydrocarbon groups having 1 to 16 carbon atoms are preferred. The alkyl groups may be straight-chain or branched. Preferred examples of the alkyl groups include lower alkyl groups having 1 to 6 carbon atoms, such as methyl, ethyl, propyl, i-propyl, butyl, i-butyl, t-butyl, pentyl, and hexyl. Preferred examples of the alkenyl groups include alkenyl groups having 2 to 6 carbon atoms, such as vinyl, allyl, 1-propenyl, i-propenyl, 2-butenyl, 1,3-butadienyl and 2-pentenyl. Preferred examples of the alkynyl groups include alkynyl groups having 2 to 6 carbon atoms, such as ethynyl and 2-propynyl. The cycloalkyl groups are preferably cycloalkyl groups having 3 to 6 carbon atoms, such as cyclopropyl, cyclobutyl, cyclopentyl and cyclohexyl. Preferred examples of the aryl groups include aryl groups having 6 to 14 carbon atoms, such as phenyl, 1-naphthyl, 2-naphthyl, biphenylyl, 2-indenyl and 2-anthryl. Preferred examples of the aralkyl groups include alkyl groups having 1 to 6 carbon atoms substituted by the above-mentioned aryl groups (e.g., $C_{6-10}$ aryl), such as $C_{6-10}$ aryl-$C_{1-6}$ alkyl groups (e.g., benzyl, phenethyl, naphthylmethyl).

The substituents which these hydrocarbon groups may have are not specifically limited so long as the objective of the present invention can be achieved, and any substituents that can commonly be used in medicines can be used. Examples of the substituents include hydroxyl; $C_{1-3}$ alkoxy (e.g., methoxy, ethoxy, n-propoxy, iso-propoxy); aralkyloxy (e.g., $C_{6-10}$ aryl-$C_{1-6}$ alkyloxy such as phenyl-$C_{1-6}$ alkyloxy, naphthyl-$C_{1-6}$ alkyloxy, for example, benzyloxy, phenetyloxy); aryloxy (e.g., $C_{6-10}$ aryloxy such as phenyloxy, naphthyloxy); heteroaryloxy (e.g., 5- to 10-membered heteroaryloxy such as pyridyloxy, imidazolyloxy); mercapto; $C_{1-3}$ alkylthio (e.g., methylthio, ethylthio); $C_{1-3}$ alkylsulfonyl (e.g., mesyl, ethylsulfonyl); $C_{1-3}$ alkylsulfinyl (e.g., methylsulfinyl, ethylsulfinyl); aralkylthio (e.g., $C_{6-10}$ aryl-$C_{1-6}$ alkylthio such as phenyl-$C_{1-6}$ alkylthio, naphthyl-$C_{1-6}$ alkylthio, for example, benzylthio, phenethylthio); aralkylsulfonyl (e.g., $C_{6-10}$ aryl-$C_{1-6}$ alkylsulfonyl such as phenyl-$C_{1-6}$ alkylsulfonyl, naphthyl-$C_{1-6}$ alkylsulfonyl, for example, benzylsulfonyl, phenethylsulfonyl); aralkylsulfinyl (e.g., $C_{6-10}$ aryl-$C_{1-6}$ alkylsulfinyl such as phenyl-$C_{1-6}$ alkylsulfinyl, naphthyl-$C_{1-6}$ alkylsulfinyl, for example, benzylsulfinyl, phenethylsulfinyl); arylthio (e.g., $C_{6-10}$ arylthio such as phenylthio, naphthylthio); heteroarylthio (e.g., 5- to 10-membered heteroarylthio such as pyridylthio, imidazolylthio); arylsulfonyl (e.g., $C_{6-10}$ arylsulfonyl such as phenylsulfonyl, naphthylsulfonyl); heteroarylsulfonyl (e.g., 5- to 10-membered heteroarylsulfonyl such as pyridylsulfonyl, imidazolylsulfonyl); arylsulfinyl (e.g., $C_{6-10}$ arylsulfinyl such as phenylsulfinyl, naphthylsulfinyl); heteroaylsulfinyl (e.g., 5- to 10-membered heteroarylsulfinyl such as pyridylsulfinyl, imidazolylsulfinyl); amino; mono- or di-substituted amino substituted by one or two groups selected from $C_{1-3}$ alkyl, aralkyl (e.g., $C_{6-10}$ aryl-$C_{1-6}$ alkyl such as phenyl-$C_{1-6}$ alkyl, naphthyl-$C_{1-6}$ alkyl), aryl (e.g., $C_{6-10}$ aryl such as phenyl, naphthyl) and heteroaryl (e.g., 5- to 10-membered heteroaryl such as pyridyl, imidazolyl) (e.g., methylamino, ethylamino, dimethylmino, benzylamino, phenylamino, pyridylamino); halogen (e.g., chloro, fluoro, bromo); esterified carboxyl (e.g., $C_{1-4}$ alkoxy-carbonyl such as methoxycarbonyl, ethoxycarbonyl); $C_{2-3}$ acyl (e.g., $C_{2-3}$ alkanoyl such as acetyl, propionyl); $C_{2-3}$ acyloxy (e.g., $C_{2-3}$ alkanoyloxy such as acetoxy, propionyloxy); $C_{2-3}$ acylamido (e.g., $C_{2-3}$ alkanoylamido such as acetamido); $C_{1-4}$ alkoxy-carbonylamino (e.g., methoxycarbonylamino, ethoxycarbonylamino); cyclic amino groups (e.g., 3- to 6-membered cyclic amino such as pyrrolidino, morpholino, piperazino); carboxyl; and carbamoyl. The number of these substituent(s) is 1 to 5, preferably 1 to 2. When the number of the substituent is two or more, each substituent may be the same as or different from one another.

The hydrocarbon ring of the optionally substituted hydrocarbon ring represented by $R^2$ and $R^3$ include, for example, aromatic hydrocarbon rings having 6 to 14 carbon atoms (e.g., benzene ring, naphthalene ring, anthracene ring, phenanthrene ring, azulene ring), and cycloalkene having 5 to 8 carbon atoms (e.g., cyclopentene, cyclopentadiene, cyclohexene, cyclohexadiene). Among them, a 5- or 6-membered hydrocarbon ring is preferred. In particular, a benzene ring is preferred. Examples of the substituents which the hydrocarbon ring may have include alkyl groups having 1 to 3 carbon atoms (e.g., methyl, ethyl, propyl), alkoxy groups having 1 to 3 carbon atoms (e.g., methoxy, ethoxy, propoxy), hydroxyl, halogen and amino. The number of the substituent(s) is preferably 1 to 3. When the number of the substituent is two or more, each substituent may be the same as or different from one another.

$R^1$ is preferably $C_{1-6}$ alkyl or $C_{1-6}$ alkoxy, more preferably $C_{1-6}$ alkyl, particularly methyl.

Preferably, $R^2$ and $R^3$ are independently $C_{1-6}$ alkyl or $C_{1-6}$ alkoxy, more preferably methyl or methoxy.

The alkyl groups represented by $R^4$ include, for example, straight-chain, branched or cyclic alkyl groups having 1 to 6 carbon atoms, such as methyl, ethyl, propyl, i-propyl, butyl, i-butyl, t-butyl, pentyl, hexyl, cyclopropyl, cyclobutyl and cyclopentyl.

$R^4$ is preferably $C_{1-6}$ alkyl, more preferably $C_{1-3}$ alkyl, in particular, methyl.

The substituents which the optionally substituted hydroxyl group represented by $R^5$ may have include groups that can commonly be used as protective groups of a hydroxyl group. Examples of the substituents include $C_{1-6}$ alkyl (e.g., methyl, ethyl, n-propyl, isopropyl, butyl, tert-butyl), $C_{6-10}$ aryl (e.g., phenyl), $C_{7-10}$ aralkyl (e.g., benzyl), $C_{1-6}$ alkyl-carbonyl (e.g., acetyl, propionyl), $C_{6-10}$ aryl-carbonyl (e.g., benzoyl), $C_{7-10}$ aralkyl-carbonyl (e.g., benzylcarbonyl), tetrahydropyranyl and tetrahydrofuranyl groups. The above $C_{1-6}$ alkyl, $C_{6-10}$ aryl, $C_{7-10}$ aralkyl, $C_{1-6}$ alkyl-carbonyl, $C_{6-10}$ aryl-carbonyl, $C_{7-10}$ aralkyl-carbonyl, tetrahydropyranyl and tetrahydrofuranyl may be substituted by 1 to 3 substituents selected from the group consisting of halogen atoms (e.g., fluorine, chlorine, bromine, iodine), $C_{1-6}$ alkyl (e.g., methyl, ethyl, n-propyl), $C_{6-10}$ aryl (e.g., phenyl), $C_{7-10}$aralkyl (e.g., benzyl) and nitro. The above formyl and silyl may be substituted by 1 to 3 substituents selected from the group consisting of $C_{1-6}$ alkyl, $C_{6-10}$ aryl and $C_{7-10}$ aralkyl.

$R^5$ is preferably hydroxyl.

The hydrocarbon groups of the optionally substituted hydrocarbon groups represented by $R^6$ or $R^7$ include, for example, the hydrocarbon groups represented by $R^1$, $R^2$ and $R^3$. The hydrocarbon groups are preferably alkyl groups having 1 to 6 carbon atoms. The substituents which the hydrocarbon groups represented by $R^6$ or $R^7$ may have include, for example, substituents which the hydrocarbon groups represented by $R^1$, $R^2$ and $R^3$ may have, and optionally substituted aromatic groups. The optionally substituted aromatic groups include, for example, the optionally substituted aromatic groups described above as the substituents of the optionally substituted amino group represented by $R^1$, $R^2$ and $R^3$.

$R^6$ and $R^7$, taken together with the adjacent nitrogen atom, may form an optionally substituted ring. The rings of the optionally substituted rings include, for example, 3- to 7-membered N-containing heterocyclic rings, preferably saturated 3- to 7-membered nitrogen-containing heterocyclic rings, which may contain, besides carbon atoms and a nitrogen atom, 1 to 3 hetero atoms selected from nitrogen, oxygen and sulfur atoms. Examples of the heterocyclic rings include aziridine, piperidine, morpholine, thiomorpholine, piperazine, azetidine, 2-oxoazetidine, 2-oxopyrrolidine and 2-oxopiperidine. In particular, 6-membered nitrogen-containing heterocyclic rings are preferred, and piperidine is particularly preferred.

The substituents of the optionally substituted rings include, for example, the substituents of the optionally substituted aromatic groups described above. The number of the substituent(s) is not specifically limited, and it is 1 to 5, preferably 1 to 3. Preferred examples of the substituents include $C_{6-14}$ aryl groups, in particular, phenyl.

When $R^6$ and $R^7$ independently represent an optionally substituted hydrocarbon group, $R^2$ and $R^3$ preferably independently represent an optionally substituted alkoxy group.

m is preferably 1.

n is preferably 1 or 5, more preferably 1.

The hydroquinone derivatives of the compound of the formula (I) include, for example, a compound of the formula (I'):

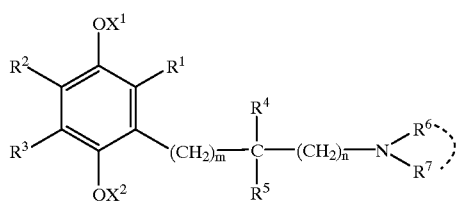

(I')

wherein $X^1$ and $X^2$ independently represent hydrogen, an optionally substituted hydrocarbon group, an optionally substituted aromatic group or an acyl group, and the other symbols are as defined above, or a salt thereof.

The optionally substituted hydrocarbon groups represented by $X^1$ or $X^2$ include those represented by $R^1$, $R^2$ or $R^3$. Preferred examples of the hydrocarbon groups include alkyl, alkenyl, alkynyl, cycloalkyl and aralkyl. The optionally substituted aromatic groups represented by $X^1$ or $X^2$ include the optionally substituted aromatic groups (e.g., phenyl) described above as the substituents which the amino group represented by $R^1$, $R^2$ or $R^3$ may have.

The acyl groups represented by $X^1$ or $X^2$ include acyl groups having 2 to 6 carbon atoms, for example, $C_{2-6}$ alkanoyl, preferably $C_{1-5}$ alkyl-carbonyl such as acetyl, propionyl, butyryl, isobutyryl and valeryl, a D-glucuronyl group and a sulfonyl group. Among them, preferred is $C_{1-5}$ alkyl-carbonyl.

Preferably, $X^1$ and $X^2$ are independently hydrogen, $C_{1-6}$ alkyl and $C_{1-5}$ alkyl-carbonyl. In particular, hydrogen is preferred.

Preferred examples of each symbol in the formula (I') are the same as those for the formula (I).

The compound (I) and its hydroquinone derivative can readily be interconverted to each other by, for example, chemical or biochemical oxidation or reduction of the quinone and hydroquinone nuclei. Since the hydroquinone derivative is, in general, readily oxidized with oxygen, air, etc., it is usually handled as the corresponding stable quinone compound. Since the quinone compound and its hydroquinone derivative can readily be interconverted to each other by chemical or biochemical oxidation or reduction, the quinone compound and its hydroquinone derivative can be considered to have equivalent properties when they exhibit pharmacological activity under physiological conditions.

The compound of the present invention is preferably the compound (I) or (I') wherein $R^1$, $R^2$ and $R^3$ are an alkyl group having 1 to 6 carbon atoms;

$R^4$ is an alkyl group having 1 to 3 carbon atoms;

$R^5$ is a hydroxyl group;

$R^6$ and $R^7$ are joined together to form a 6-membered nitrogen-containing heterocyclic ring (in particular, piperidine) optionally substituted by a $C_{6-14}$ aryl group; and m and n are 1.

Also preferred is a compound (I) or (I') wherein $R^1$ is $C_{1-6}$ alkyl, $R^2$ and $R^3$ are independently $C_{1-6}$ alkyl or $C_{1-6}$ alkoxy, R is $C_{1-6}$ alkyl, R is hydroxyl, R and R taken together with the adjacent nitrogen atom, form a 6-membered N-containing heterocyclic ring optionally containing, besides carbon atoms and a nitrogen atom, 1 to 3 hetero atoms selected from nitrogen atom and oxygen atom, which ring may be substituted by a $C_{6-14}$ aryl, m is 1, and n is 1 or 5.

Preferred examples of the compound (I) include 2-[2-hydroxy-2-methyl-3-(4-phenylpiperidin-1-yl)propyl]-3,5,6-trimethyl-1,4-benzoquinone, 2-[2-hydroxy-2-methyl-3-(4-phenylpiperidin-1-yl)propyl]-5,6-dimethoxy-3-methyl-1,4-benzoquinone, 2-(2-hydroxy-2-methyl-7-morpholinoheptyl)-5,6-dimethoxy-3-methyl-1,4-benzoquinone and salts thereof. More preferred examples thereof include (S)-2-[2-hydroxy-2-methyl-3-(4-phenylpiperidin-1-yl)propyl]-3,5,6-trimethyl-1,4-benzoquinone of the formula (A):

maleic acid, citric acid, malic acid, methanesulfonic acid, benzenesulfonic acid and p-toluenesulfonic acid. Preferred examples of the salts with basic amino acids include salts with arginine, lysine and ornithine. Preferred examples of the salts with acidic amino acids include salts with aspartic acid and glutamic acid.

In particular, pharmaceutically acceptable salts are preferred. When the compound (I) or (I') has a basic functional group in the molecule, it can form salts with inorganic acids such as hydrochloric acid, hydrobromic acid, nitric acid, sulfuric acid and phosphoric acid and salts with organic acids such as acetic acid, phthalic acid, fumaric acid, tartaric acid, maleic acid, citric acid, methanesulfonic acid and p-toluenesulfonic acid. When the compound (I) or (I') has an acidic functional group in the molecule, it can form salts with alkaline metals such as sodium and potassium, salts with alkaline earth metals such as calcium and magnesium, a salt with ammonium, etc.

The compound (I), (I') or a salt thereof may be an anhydrate (i.e., water-free form) or hydrate thereof.

The compound (I), (I') or a salt thereof (hereinafter abbreviated as the compound (I) or (I')) can be produced as follows.

The compound (I) of the present invention can be produced by the per se known method, for example, the method shown in the following reaction scheme or modified methods thereof. In the following scheme, Z is an alkyl group (e.g., $C_{1-6}$ alkyl group) or hydrogen, and the other symbols are as defined above.

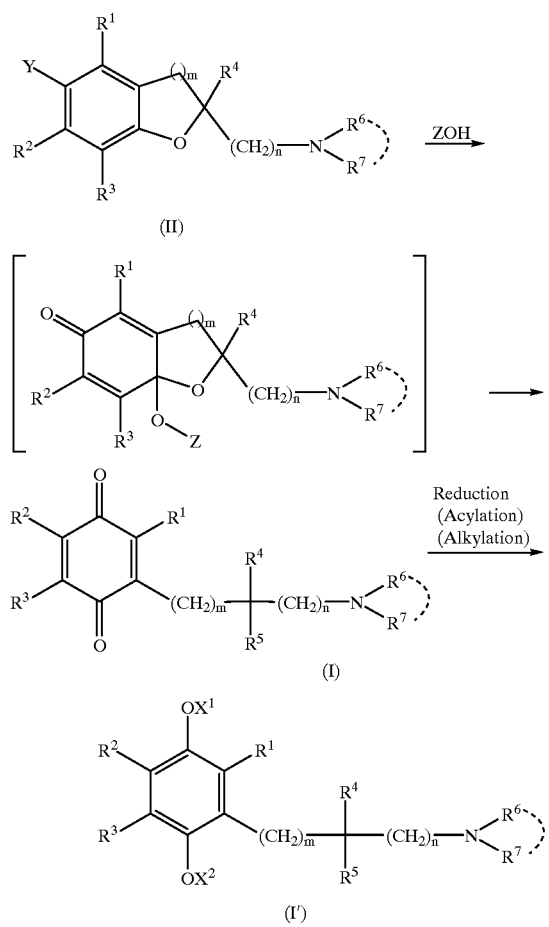

The compound (II), wherein Y represents —$NR^8R^9$ or —$OR^{10}$ wherein $R^8$, $R^9$ and $R^{10}$ independently represent hydrogen, an optionally substituted hydrocarbon group or an acyl group, and the other symbols are as defined above, in the above scheme includes its salts. The salts includes, for example, the salts of the compound (I). The compound (II) can be produced by per se known methods, for example, the methods described in JP-A 5-140142, JP-A 6-41123, JP-A 6-228136, etc., or modified methods thereof.

The optionally substituted hydrocarbon groups and the acyl groups represented by $R^8$, $R^9$ or $R^{10}$ include, for example, the optionally substituted hydrocarbon groups and the acyl groups represented by $X^1$ or $X^2$ described above, respectively.

The compound (I) can be produced by subjecting the compound (II) to per se known oxidation. The oxidizing agents to be used in this reaction include radicals such as Fremy salt (($KSO_3)_2NO$), galvinoxyl and 2,2-di(4-tert-octylphenyl)-1-picrylhydrazyl (DPPH), chromic acids such as chromic anhydride ($CrO_3$), sodium dichromate ($Na_2Cr_2O_7$) and potassium dichromate ($K_2Cr_2O_7$), periodates such as paraperiodic acid ($H_5IO_6$), metaperiodic acid ($HIO_4$) and sodium metaperiodate ($NaIO_4$), metal oxides such as manganese dioxide ($MnO_2$), silver oxide ($Ag_2O$), lead dioxide ($PbO_2$) and divanadium pentaoxide ($V_2O_5$), peroxides such as hydrogen peroxide ($H_2O_2$) and tert-butylhydroperoxide ($^tBuOOH$), gases such as oxygen (including photooxidation) and air (including photooxidation), mineral

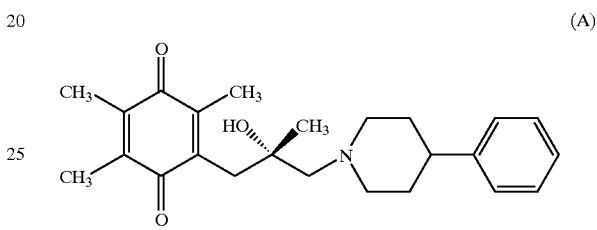

(A)

The salts of the compound (I) or (I') include salts used as synthetic intermediates and pharmaceutically acceptable salts. Examples of the salts include salts with inorganic bases, salts with organic bases, salts with inorganic acids, salts with organic acids, and salts with basic or acidic amino acids. Preferred examples of the salts with inorganic bases include salts with alkaline metals such as sodium and potassium, salts with alkaline earth metals such as calcium and magnesium, aluminium salts, and ammonium salts. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Preferred examples of the salts with inorganic acids include salts with hydrochloric acid, hydrobromic acid, nitric acid, sulfuric acid and phosphoric acid. Preferred examples of the salts with organic acids include salts with formic acid, acetic acid, trifluoroacetic acid, phthalic acid, fumaric acid, oxalic acid, tartaric acid, acids such as nitric acid and sulfuric acid, and metal salts such as lead tetraacetate ($Pb(OAc)_4$) and ferric chloride ($FeCl_3$). The amount of the oxidizing agent to be used is about 2 to 30 mol, preferably about 2 to 10 mol, per mol of the compound (II).

These reactions may be carried out in the presence of a base. Examples of the bases include inorganic bases such as sodium hydroxide, potassium hydroxide, potassium carbonate, sodium carbonate and sodium bicarbonate, metal alkolates such as sodium methoxide, sodium ethoxide and potassium tert-butoxide, and organic bases such as triethylamine, imidazole and formamidine. The amount of the base to be used is about 0.5 to 30 mol, preferably about 0.5 to 10 mol, per mol of the compound (II).

Any solvent can be used so long as the reaction can proceed. Preferred examples of the solvents include compounds of the formula ZOH, wherein Z is an alkyl group or hydrogen, such as alcohols (ZOH wherein Z is an alkyl group) (e.g., methanol, ethanol, propanol), water (ZOH wherein Z is hydrogen) and mixtures thereof, or mixtures thereof with ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, ketones such as acetone and methyl ethyl ketone, and sulfoxides such as dimethyl sulfoxide.

The reaction time is normally 30 minutes to 48 hours, preferably 30 minutes to 5 hours. The reaction temperature is normally −20 to 200° C., preferably −10 to 150° C.

The compound (I) thus produced can be isolated from the reaction mixture by conventional methods, and easily purified by conventional separation techniques such as recrystallization, distillation and chromatography. The compound (I) has stereoisomers. Not only each stereoisomer but also mixtures thereof are included in the scope of the present invention. If necessary, the reaction intermediate can be isolated.

If necessary, the resultant oxidation product may be subjected to any one or more of protection, reduction, acylation, alkylation, oxidation, hydrogenation, carbon-chain extension, substitution and deprotection. These reactions can be carried out by the per se known methods, for example, the methods described in, for example, Shin Jikken Kagaku Koza, Vol. 14, 15, compiled by The Chemical Society of Japan, published in 1977, 1978, etc., or modified methods thereof.

The compound (I) can be converted to the compound (I') by optionally reducing the quinone moiety, followed by acylation or alkylation. The reducing agents to be used in the reduction include, for example, metals or metal salts such as zinc—sodium hydroxide, zinc—acetic acid, and tin (II) chloride—hydrochloric acid, metal hydrides such as diisobutyl aluminum hydride and hydrosilane, metal hydride complexes such as lithium aluminum hydride and sodium borohydride, sodium dithionite, and diborane. In place of reducing agents, metal catalysts such as palladium-carbon, platinum oxide, Raney-nickel and Raney-cobalt can be used to conduct catalytic reduction. The amount of the reducing agent to be used is about 0.5 to 30 mol, preferably about 0.5 to 10 mol, per mol of the compound (I). The amount of the catalyst to be used in the catalytic reduction is about 5 to 300% by weight based on the compound (I).

The reaction can advantageously be carried out in the absence of a solvent or in a solvent inert to the reaction. Any solvent can be used so long as the reaction can proceed. Examples of the solvents include alcohols such as methanol, ethanol and propanol, ethers such as diethyl ether, tetrahydrofuran, dioxane and 1,2-dimethoxyethane, hydrocarbons such as benzene, toluene, cyclohexane and hexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, ketones such as acetone and methyl ethyl ketone, sulfoxides such as dimethyl sulfoxide, and water, and mixed solvents of these two or more solvents.

The reaction time is normally 30 minutes to 48 hours, preferably 30 minutes to 5 hours. The reaction temperature is normally −20 to 150° C., preferably −10 to 100° C.

When acylation is carried out after the reduction, the hydroquinone (hydroquinone compound) of the compound (I) or its salt thus obtained is reacted with a carboxylic acid [e.g., the compound of the formula $X^1$—OH or $X^2$—OH (in case $X^1$ and $X^2$ are independently acyl)], a salt thereof or a reactive derivative thereof. The reactive derivatives of the carboxylic acids include, for example, acid halides (e.g., acid chloride, acid bromide), acid amides (e.g., acid amides with pyrazole, imidazole, benzotriazole), and acid anhydrides (e.g., $C_{1-6}$ aliphatic acid anhydrides such as acetic anhydride, propionic anhydride, butyric anhydride). The amount of the carboxylic acid, the salt thereof or the reactive derivative thereof to be used is normally about 1 to 5 mol, preferably about 1 to 3 mol, per mol of the above hydroquinone compound.

This reaction can advantageously be carried out using a solvent inert to the reaction. Any solvent can be used so long as the reaction can proceed. Examples of the solvents include ethers such as diethyl ether, tetrahydrofuran, dioxane and 1,2-dimethoxyethane, hydrocarbons such as benzene, toluene and cyclohexane, amides such as N,N-dimethylformamide and N,N-dimethylacetamide, halogenated hydrocarbons such as dichloromethane, chloroform, carbon tetrachloride and 1,2-dichloroethane, nitrites such as acetonitrile and propionitrile, and mixed solvents of these two or more solvents.

When an acid halide is used as the reactive derivative of a carboxylic acid, the reaction can be carried out in the presence of an acid-removing agent to remove the released hydrogen halide from the reaction system. Preferred examples of the acid-removing agents include inorganic bases such as sodium carbonate, potassium carbonate and sodium bicarbonate, and tertiary amines such as triethylamine, tripropylamine, tributylamine, cyclohexyldimethylamine, pyridine, 4-dimethylaminopyridine, lutidine, N,N-dimethylaniline, N-methylpiperidine, N-methylpyrrolidine and N-methylmorpholine.

The reaction time varies with the reagent or solvent to be used, but is normally 30 minutes to 24 hours, preferably 30 minutes to 4 hours. The reaction temperature is normally 0 to 100° C., preferably 0 to 70° C.

When alkylation is carried out after the reduction, the hydroquinone compound is reacted with an alkylating agent such as an alkyl halide, a sulfonic acid ester of an alcohol (e.g., methanesulfonic acid ester, p-toluenesulfonic acid ester) or an alcohol itself. The amount of the alkylating agent to be used is about 1 to 10 mol, preferably about 1 to 3 mol, per mol of the hydroquinone compound. When an alkyl halide or a sulfonic acid ester of an alcohol is used, the reaction is carried out in the presence of a base. Examples of the bases include metal hydrides such as sodium hydride and potassium hydride, metal alkolates such as sodium methylate, sodium ethylate and potassium tert-butoxide, metal amides such as sodium amide, lithium diisopropylamide and lithium hexamethyldisilazide, and inorganic bases such as potassium carbonate, sodium carbonate, sodium hydroxide and potassium hydroxide. The amount of the base to be used is about 1 to 5 mol, preferably about 1 to 3 mol, per mol of the hydroquinone compound.

This reaction can advantageously be carried out using a solvent inert to the reaction. Any solvent can be used so long as the reaction can proceed. Preferred examples of the solvents include benzene, dimethylformamide, tetrahydrofuran, hexamethylphosphoric triamide, dimethyl sulfoxide, 1,2-dimethoxyethane and mixed solvents thereof.

The reaction time is normally 1 hour to 24 hours, preferably 1 hour to 6 hours. The reaction time is normally 0 to 150° C., preferably 0 to 100° C.

When an alcohol is used as the alkylating agent, an acid is used as a catalyst. Examples of the acids include Lewis acids such as boron trifluoride etherate and aluminium chloride. The amount of the acid to be used is 1 to 10 mol, preferably 1 to 5 mol, per mol of the hydroquinone compound.

The reaction time is normally 1 to 24 hours, preferably 1 to 6 hours. The reaction temperature is normally 0 to 150° C., preferably 0 to 100° C.

Any solvent can be used for the reaction so long as the reaction can proceed. Preferred examples of the solvents include alcohols such as methanol and ethanol, ethers such as ether and tetrahydrofuran, aromatic hydrocarbons such as benzene and toluene, aliphatic hydrocarbons such as hexane and cyclohexane, and mixed solvents thereof.

The compound (I') thus obtained can be isolated from the reaction mixture by conventional methods, and easily purified by conventional separation techniques such as recrystallization, distillation and chromatography.

The compound (I') has stereoisomers. Not only each stereoisomer but also mixtures thereof are included in the scope of the present invention.

If necessary, the above reactions can be combined with one or more of known protection, reduction, acylation, alkylation, oxidation, hydrogenation, carbon-chain extension, substitution and deprotection to produce compound (I'). These reactions can be carried out by the methods described in, for example, Shin Jikken Kagaku Koza, Vol. 14, 15, compiled by The Chemical Society of Japan, published in 1977, 1978, etc., or modified methods thereof.

In each process of the present invention and each reaction for synthesizing the starting compound described above, when the starting compound has an amino, carboxyl or hydroxyl group as a substituent, these groups may be protected with a protective group commonly used in peptide synthesis, which may be removed after the reactions to obtain the desired compound.

The protective groups for an amino group include, for example, formyl, $C_{1-6}$ alkyl-carbonyl groups (e.g., acetyl, propionyl), $C_{1-6}$ alkyloxycarbonyl groups (e.g., methoxycarbonyl, ethoxycarbonyl), benzoyl, $C_{7-10}$ aralkyl-carbonyl groups (e.g., benzylcarbonyl), trityl, phthaloyl, and N,N-dimethylaminomethylene. These groups may be substituted by 1 to 3 substituents selected from halogen atoms (e.g., fluorine, chlorine, bromine, iodine) and nitro.

The protective groups for a carboxyl group include, for example, $C_{1-6}$ alkyl groups (e.g., methyl, ethyl, propyl, isopropyl, butyl, tert-butyl), phenyl, trityl and silyl. These groups may be substituted by 1 to 3 substituents selected from halogen atoms (e.g., fluorine, chlorine, bromine, iodine), formyl, C1-6 alkyl-carbonyl groups (e.g., acetyl, propionyl, butyryl) and nitro.

The protective groups for a hydroxyl group include, for example, $C_{1-6}$ alkyl groups (e.g., methyl, ethyl, propyl, isopropyl, butyl, tert-butyl), phenyl, $C_{7-10}$ aralkyl groups (e.g., benzyl), $C_{1-6}$ alkyl-carbonyl groups (e.g., acetyl, propionyl), benzoyl, $C_{7-10}$ aralkyl-carbonyl groups (e.g., benzylcarbonyl), tetrahydropyranyl, tetrahydrofuranyl, and silyl. These groups may be substituted by 1 to 3 substituents selected from halogen atoms (e.g., fluorine, chlorine, bromine, iodine), $C_{1-6}$ alkyl groups (e.g., methyl, ethyl, propyl), phenyl, $C_{7-10}$ aralkyl groups (e.g., benzyl), and nitro.

These protective groups can be removed by per se known methods or modified methods thereof, for example, by reduction or methods using acids, bases, ultraviolet light, hydrazine, phenylhydrazine, sodium N-methyldithiocarbamate, tetrabutylammonium fluoride, palladium acetate, etc.

The compound (I) of the present invention can be isolated and purified by known techniques such as solvent extraction, liquid conversion, redistribution, crystallization, recrystallization and chromatography. The starting compound of the compound (I) or its thereof can be isolated or purified by known techniques as described above. Alternatively, the reaction mixture can be used without any isolation as a starting material for the next step.

When the desired product is obtained in a free form in the above process, it can be converted to its salt by conventional methods. When the desired product is obtained as a salt, it can be converted to its free form or other salts by conventional methods. The compound (I) or (I') thus obtained can be isolated from the reaction mixture and purified by conventional techniques such as redistribution, concentration, solvent extraction, fractional distillation, crystallization, recrystallization and chromatography.

When the compound (I) or (I') exists as configurational isomers, diastereomers, conformers, etc., they can be isolated from each other by the above separation and purification techniques. When the compound (I) or (I') is optically active, the d- and l-isomers can be separated from each other by conventional optical resolution.

The compound (I) or (I') of the present invention has improving effect on the metabolism of poly unsaturated fatty acids (e.g., linoleic acid, γ-linolenic acid, α-linolenic acid, arachidonic acid, dihomo-γ-linolenic acid, eicosapentaenoic acid), particularly inhibitory effect on lipoperoxide formation (antioxidative effect), inhibitory effect on the formation of 5-lipoxygenase metabolites [e.g., leukotrienes, 5-hydroperoxyeicosatetraenoic acid (HPETE), 5-hydroxyeicosatetraenoic acid (HETE), lipoxins, leukotoxines], inhibitory effect on thromboxane $A_2$-synthetase, maintaining and enhancing effect on prostaglandin $I_2$-synthetase, $LTD_4$ receptor antagonism, scavenging effect on active oxygen species, sodium channel blocking effect, improving effect on central nervous system disorders based on dopamine abnormal release inhibitory effect, improving effect on the circulatory system, antiallergic effect, etc.

In particular, the compound (I) or (I') of the present invention shows significant lipoperoxide formation inhibitory effect (antioxidative effect) and significant sodium channel blocking effect.

The compound (I) or (I') is less in toxicity and has little side effect.

Therefore the compound (I) or (I') of the present invention has therapeutic and prophylactic effects on various diseases in mammals (e.g., mice, rats, rabbits, dogs, monkeys, humans) such as thrombosis caused by platelet aggregation; ischemic diseases caused by constriction of arterial vascular smooth muscle or vasospasm in the heart, lung, brain and kidney (e.g., myocardial infarction, cerebral infarction, cerebral apoplexy); neuropathy (e.g., Parkinson's disease, Alzheimer's disease, Lou-Gehring's disease, muscular dystrophy); neurological disorders caused by central nervous system damage such as cranial injury and spinal injury; dysmnesia or emotional disturbance (disorders accompanied by nerve cell necrosis caused by hypoxia, cerebral lesion, cerebral apoplexy, cerebral hemorrhage, cerebral infarction, cerebral thrombosis); convulsion and epilepsy caused after cerebral apoplexy, cerebral infarction, cerebral surgery or cranial injury; nephritis; pulmonary insufficiency; bronchial asthma; inflammation; arterial sclerosis; atherosclerosis; hepatitis; acute hepatitis; cirrhosis; hypersensitive hepatitis; immunodeficiency syndrome; circulatory diseases caused by damages to enzymes, tissue, cells, etc., of the living body due to active oxygen species (e.g., superoxide, hydroxy radicals) (e.g., cardiac infarction, cerebral infarction, cerebral apoplexy, cerebral edema, nephritis); tissue fibroplastic phenomenon; carcinogenesis, etc. For example, the compound (I) or (I') of the present invention is useful as medicines such as antithrombotic agents, antivasoconstriction agents, antiasthamatic agents, antiallergic agents, agents for improving the function of the circulatory system such as the heart and brain, agents for treating nephritis, agents for treating hepatitis, agents for inhibiting tissue fibrosis, agents for scavenging active oxygen species, agents for regulating and improving arachidonate cascade substances, agents for Alzheimer's disease and nootropic.

The compound (I) or (I') can safely be administered orally or parenterally as it is, or in the form of pharmaceutical compositions (e.g., tablets, capsules, solutions, injections, suppositories) prepared by mixing the compound (I) or (I') with per se known pharmaceutically acceptable carriers, excipients, etc. The content of the compound (I) or (I') in the pharmaceutical composition of the present invention is dependent on, for example, type of preparations, administration method and carriers. It usually ranges from about 0.01 to nearly 100 weight % relative to the whole weight of the composition. The dosage varies with the subject, administration route, symptoms, etc. For example, in the case of intravenous administration to an adult patient with cerebral apoplexy, it is advantageous that the compound of the present invention is administered in a dose of about 0.1 mg/kg to 30 mg/kg of body weight, preferably 0.5 mg/kg to 10 mg/kg of body weight about 1 to 3 times per day.

The pharmaceutically acceptable carrier which may be used to produce the composition of the present invention include various organic or inorganic carrier materials commonly used in pharmaceutical preparations, such as excipients, lubricants, binders and disintegrators for solid preparations, and solvents, solution adjuvants, suspending agents, tonicity agents, buffering agents and soothing agents for liquid preparations. If necessary, additives such as antiseptics, antioxidants, colorants, sweetening agents, adsorbents and wetting agents can be used.

Examples of the excipients include lactose, sucrose, D-mannitol, starch, corn starch, crystalline cellulose and light anhydrous silicic acid.

Examples of the lubricants include magnesium stearate, calcium stearate, talc and colloidal silica.

Examples of the binders include crystalline cellulose, sucrose, D-mannitol, dextrin, hydroxypropylcellulose, hydroxypropylmethylcellulose, polyvinyl-pyrrolidone, starch, sucrose, gelatin, methylcellulose and carboxymethylcellulose sodium.

Examples of the disintegrants include starch, carboxymethylcellulose, carboxymethylcellulose calcium, croscarmellose sodium, carboxymethyl starch sodium and L-hydroxypropylcellulose.

Examples of the solvents include water for injection, alcohols, propylene glycol, macrogol, sesame oil and corn oil.

Examples of the solubilizers include polyethylene glycol, propylene glycol, D-mannitol, benzyl benzoate, ethanol, trisaminomethane, cholesterol, triethanolamine, sodium carbonate and sodium citrate.

Examples of the suspending agents include surfactants such as stearyl triethanolamine, sodium lauryl sulfate, laurylaminopropionic acid, lecithin, benzalkonium chloride, benzethonium chloride and glyceryl monostearate; and hydrophilic polymers such as polyvinyl alcohol, polyvinyl-pyrrolidone, carboxymethylcellulose sodium, methylcellulose, hydroxymethylcellulose, hydroxyethylcellulose and hydroxypropylcellulose.

Examples of the isotonizing agents include glucose, D-sorbitol, sodium chloride, glycerin and D-mannitol.

Examples of the buffering agents include buffers such as phosphates, acetates, carbonates and citrates.

Examples of the soothing agents include benzyl alcohol.

Examples of the antiseptics include parahydroxy-benzoic acid esters, chlorobutanol, benzyl alcohol, phenethyl alcohol, dehydroacetic acid and sorbic acid.

Examples of the antioxidants include sulfites, ascorbic acid and α-tocopherol.

EXAMPLES

The following experiments, reference examples, examples and preparations further illustrate the present invention in detail, but are not to be construed to limit the scope thereof. "%" in the following Reference Examples and Examples means weight % unless otherwise specified. The term "room temperature" means 10 to 30° C.

Other abbreviations employed in the description have the following meanings.

s: singlet
d: doublet
t: triplet
q: quartet
m: multiplet
br: broad
J: coupling constant
Hz: Herz
$CDCl_3$: deuterochloroform
$DMSO-d_6$: (dimethyl sulfoxide)-$d_6$
$^1H$-NMR: proton nuclear magnetic resonance

Experiment 1

Lipoperoxide Formation Inhibitory Effect Methods

The lipoperoxide formed in the brain homogenate was quantified by the thiobarbituric acid (TBA) method of Stocks et al. (Cli. Sci. Mol. Med. 47, 215 (1974)). The cerebral cortex was removed from Wistar male rats (10 weeks old), and homogenized in ice-cooled phosphate physiological saline buffer (40 mM $KH_2PO_4/K_2HPO_4$, 0.142M NaCl, pH 7.4). The homogenate was centrifuged at 1,000×g for 10 minutes, and the supernatant of the homogenate was used for the experiment. A solution of the test compound in ethanol (10 μl) was added to the supernatant (1 ml), and the mixture was incubated at 37° C. for 30 minutes. The reaction was stopped by adding 35% perchloric acid solution (200 μl). The reaction mixture was centrifuged at 13,000× g for 10 minutes, and 1% thiobarbituric acid solution (250 μl) was added to the supernatant (1.0 ml). The mixture was heated at 100° C. for 15 minutes, and then the amount of malondialdehyde formed by decomposition of the lipoperoxide was determined by colorimetry (532 nm).

Results:

The $IC_{50}$ of the compound of the above formula (A) (hereinafter referred to as the compound (A)) was 3.5±0.56 μM, and the $IC_{50}$ of vitamin E was 203±43 μM.

The results clearly show that the compound (A) of the present invention has excellent lipoperoxide formation inhibitory effect.

Experiment 2

Binding affinity for $Na^+$ channel (sites 1 and 2)
Methods

The forebrain of SD male rats (7 to 8 weeks old) was used. The tissue was homogenized in a 10-fold (v/w) amount of 50 mM HEPES buffer (choline chloride 130, glucose 5.5, MgSO$_4$ 0.8, KCl 5.5 mM, pH 7.4). The homogenate was centrifuged at 1,000×g for 15 minutes. The supernatant of the homogenate was used for the experiment. The binding assay to site 1 was carried out by adding the test drug (each 25 μl), [$^3$H]-saxitoxin (final concentration: 2 nM) and the tissue homogenate (200 μl) and incubating the mixture at 37° C. for 30 minutes. The biding assay to site 2 was carried out by adding the test drug (each 25 μl), [$^3$H]-batrachotoxin (final concentration: 2 nM) and the tissue homogenate (200 μl) and incubating the mixture at 37° C. for 45 minutes. The reaction mixture was filtered with suction through Watman GF/C filter to stop the reaction. The filter was washed with 5 mM HEPES buffer (choline chloride 163, CaCl$_2$ 1.8, MgSO$_4$ 0.8 mM, pH 7.4) (10 ml). The nonspecific binding to site 1 was assayed in the presence of 1.0 μM tetrodotoxin, and the nonspecific binding to site 2 was assayed in the presence of 200 μM aconitine. The radioactivity was measured with a liquid scintillation counter (Beckman, LS3801).

Results:

The compound (A) had no effect on site 1 of Na channels, and had an IC$_{50}$ of 0.9 M. The results clearly show that the compound (A) of the present invention is a sodium channel blocker of a quite different type from the toxin tetrodotoxin.

Reference Example 1

1,4-Diacetoxy-5,6-dimethoxy-2-methylbenzene

Zinc (11 g) was added to a solution (120 ml) of coenzyme Q$_0$ (25 g) and acetic anhydride (39 ml) in pyridine, and the mixture was stirred for 30 minutes. After the reaction mixture was filtered, the filtrate was concentrated under reduced pressure. 1N hydrochloric acid was added to the residue, and the mixture was extracted with ethyl acetate. The extract was washed with saturated brine and dried over anhydrous magnesium sulfate, and the solvent was evaporated under reduced pressure. The residue was purified by column chromatography on silica gel (hexane:ethyl acetate=1:1) to obtain the title compound (31 g, 95%) as an oil.

$^1$H-NMR (CDCl$_3$) δ ppm: 2.11(3H,s), 2.32(3H,s), 2.35 (3H,s), 3.84(3H,s), 3.86(3H,s), 6.67(1H,s).

Reference Example 2

4-Acetoxy-2,3-dimethoxy-5-methylphenol

An aqueous solution (150 ml) of potassium carbonate (9.8 g) was added to a solution of 1,4-diacetoxy-5,6-dimethoxy-2-methylbenzene (31 g) in methanol (200 ml), and the mixture was stirred under an atmosphere of argon at room temperature for 1 hour. The reaction mixture was ice-cooled, made acidic by addition of hydrochloric acid (11 ml) and extracted with ethyl acetate. The extract was washed with saturated brine, dried over anhydrous magnesium sulfate and concentrated under reduced pressure to obtain the title compound (26 g, 90%) as an oil.

$^1$H-NMR (CDCl$_3$) δ ppm: 2.08(3H,s), 2.33(3H,s), 3.85 (3H,s), 3.91(3H,s), 5.58(1H,br s), 6.56(1H,s).

Reference Example 3

1-Acetoxy-2,3-dimethoxy-6-methyl-4-(2-methyl-2-propenyl)benzene

A suspension (200 ml) of 4-acetoxy-2,3-dimethoxy-5-methylphenol (26 g), methallyl chloride (13 ml) and potassium carbonate (18 g) in N,N-dimethylformamide was stirred under an atmosphere of argon at 65° C. for 15 hours. Water was added to the reaction mixture, and the mixture was extracted with ethyl acetate. The extract was washed with saturated brine and dried over anhydrous magnesium sulfate, and the solvent was evaporated under reduced pressure. The residue was purified by column chromatography on silica gel (hexane:ethyl acetate=4:1) to obtain the title compound (27 g, 84%) as an oil.

$^1$H-NMR (CDCl$_3$) δ ppm: 1.85(3H,s), 2.11(3H,s), 2.34 (3H,s), 3.87(3H,s), 3.88(3H,s), 4.44(2H,s), 5.00(1H,s), 5.12 (1H,s), 6.50(1H,s).

Reference Example 4

4-Acetoxy-2,3-dimethoxy-5-methyl-6-(2-methyl-2-propenyl)phenol

A mixture of 1-acetoxy-2,3-dimethoxy-6-methyl-4-(2-methyl-2-propenyl)benzene (27 g) and N,N-diethylaniline (200 ml) was stirred under an atmosphere of argon at 200° C. for 6 hours. After the reaction mixture was cooled, the N,N-diethylaniline was evaporated under reduced pressure. The residue was purified by column chromatography on silica gel (hexane:ethyl acetate=85:15 to 75:25) to obtain the title compound (24 g, 87%) in an amorphous form.

$^1$H-NMR (CDCl$_3$) δ ppm: 1.80(3H,s), 1.99(3H,s), 2.34 (3H,s), 3.33(2H,s), 3.84(3H,s), 3.91(3H,s), 4.43(1H,s), 4.74 (1H,s), 5.71(1H,s).

Reference Example 5

5-Acetoxy-2-bromomethyl-2,3-dihydro-6,7-dimethoxy-2,4-dimethylbenzofuran

Bromine (1.9 g) was added to a solution (40 ml) of 4-acetoxy-2,3-dimethoxy-5-methyl-6-(2-methyl-2-propenyl)phenol (3.0 g) and sodium acetate (1.0 g) in acetic acid, and the mixture was stirred at room temperature for 30 minutes. Water was added to the reaction mixture, and the mixture was extracted with ethyl acetate. The extract was washed with a saturated aqueous solution of sodium bicarbonate and saturated brine, dried over anhydrous sodium sulfate and concentrated under reduced pressure. The residue was purified by column chromatography on silica gel (hexane:ethyl acetate=85:15 to 4:1) to obtain the title compound (2.5 g, 65%) as an oil.

$^1$H-NMR (CDCl$_3$) δ ppm: 1.66(3H,s), 1.99(3H,s), 2.33 (3H,s), 2.92(1H,d,J=15.8 Hz), 3.27(1H,d,J=15.8 Hz), 3.56 (2H,s), 3.83(3H,s), 3.91(3H,s).

Reference Example 6

2-Bromomethyl-2,3-dihydro-6,7-dimethoxy-2,4-dimethylbenzofuran-5-ol

An aqueous 2.5N sodium hydroxide solution (20 ml) was added to a solution (20 ml) of 5-acetoxy-2-bromomethyl-2, 3-dihydro-6,7-dimethoxy-2,4-dimethylbenzofuran (2.5 g) in methanol (20 ml), and the mixture was stirred under an atmosphere of argon at room temperature for 1 hour. The reaction mixture was made acidic with 3N hydrochloric acid, and then extracted with ethyl acetate. The extract was washed with saturated brine, dried over anhydrous magnesium sulfate and concentrated under reduced pressure. The residue was purified by column chromatography on silica gel (hexane:ethyl acetate=85:15) to obtain the title compound (1.9 g, 87%) as an oil.

$^1$H-NMR (CDCl$_3$) δ ppm: 1.63(3H,s), 2.09(3H,s), 2.90 (1H,d,J=15.6 Hz), 3.24(1H,d,J=15.6 Hz), 3.54(2H,s), 3.90 (3H,s), 3.92(3H,s), 5.42(1H,s).

Reference Example 7

2,3-Dihydro-6,7-dimethoxy-2,4-dimethyl-2-[(4-phenylpiperidin-1-yl)methyl]benzofuran-5-ol A mixture of 2-bromomethyl-2,3-dihydro-6,7-dimethoxy-2,4-dimethylbenzofuran-5-ol (1.2 g), 4-phenylpiperidine (1.2 g) and triethylamine (1.1 ml) was stirred at under an atmosphere of argon in a sealed tube at 180° C. for 16 hours. After the reaction mixture was cooled, water, triethylamine and ethyl acetate were added, and the mixture was shaken. The organic layer was separated, washed with saturated brine, dried over anhydrous magnesium sulfate and concentrated under reduced pressure. The residue was purified by column chromatography on silica gel (hexane:ethyl acetate= 4:1) to obtain the title compound (0.6 g, 40%).

mp: 112–113° C. (recrystallized from isopropyl ether—hexane);

$^1$H-NMR (CDCl$_3$) δ ppm: 1.45(3H,s), 1.67–1.83(4H,m), 2.11(3H,s), 2.20–2.53(3H,m), 2.62(2H,s), 2.75(1H,d,J=15.2 Hz), 2.99–3.20(2H,m), 3.18(1H,d,J=15.2 Hz), 3.90(6H,s), 5.38(1H,s), 7.20–7.32(5H,m).

Reference Example 8

5-Acetoxy-2,3-dihydro-6,7-dimethoxy-2,4-dimethyl-2-benzofuranmethanol m-Chloroperbenzoic acid (32 g) was added to a solution (150 ml) of 4-acetoxy-2,3-dimethoxy-5-methyl-6-(2-methyl-2-propenyl)phenol (30 g) in dichloromethane under ice-cooling, and the mixture was stirred for 30 minutes. Triethylamine (60 ml) was added to the reaction mixture, and the mixture was stirred at room temperature for 1 hour. An aqueous solution (200 ml) of sodium hydrosulfite (4 g) was added to the reaction mixture, and the mixture was stirred for 30 minutes. The organic layer was separated, washed with saturated brine, dried over anhydrous magnesium sulfate and concentrated under reduced pressure. The residue was purified by column chromatography on silica gel (hexane:ethyl acetate=7:3 to 65:35) to obtain the title compound (25 g, 79%) as an oil.

$^1$H-NMR (CDCl$_3$) δ ppm: 1.46(3H,s), 1.98(3H,m), 2.33 (3H,s), 2.79(1H,d,J=15.2 Hz), 3.18(1H,d,J=15.2 Hz), 3.58–3.78(2H,m), 3.83(3H,s), 3.91(3H,s).

Reference Example 9

5-Acetoxy-2,3-dihydro-6,7-dimethoxy-2,4-dimethyl-2-benzofurancarbaldehyde

Dimethyl sulfoxide (2.7 ml) was added to a solution (100 ml) of oxalyl chloride (1.5 ml) in dichloromethane under an atmosphere of argon at −78° C., and the mixture was stirred for 10 minutes. A solution of 5-acetoxy-2,3-dihydro-6,7-dimethoxy-2,4-dimethyl-2-benzofuranmethanol (4.6 g) in dichloromethane (10 ml) was added, and the mixture was stirred at the same temperature for 1 hour. Triethylamine (11 ml) was added to the reaction mixture, the temperature of which was then raised to room temperature. The reaction mixture was washed with water, 1N hydrochloric acid and saturated brine, dried over anhydrous magnesium sulfate and concentrated under reduced pressure. The residue was purified by column chromatography on silica gel (hexane:ethyl acetate=3:2) to obtain the title compound (3.9 g, 86%).

$^1$H-NMR (CDCl$_3$) δ ppm: 1.59(3H,s), 1.98(3H,s), 2.33 (3H,s), 2.93(1H,d,J=15.8 Hz), 3.41(1H,d,J=15.8 Hz), 3.84 (3H,s), 3.96(3H,s), 9.77(1H,s).

Reference Example 10

Ethyl 5-(5-acetoxy-2,3-dihydro-6,7-dimethoxy-2,4-dimethylbenzofuran-2-yl)petadienoate 65% sodium hydride (0.7 g) was added to a solution (40 ml) of triethyl 4-phosphonocrotonate (4.3 g) in tetrahydrofuran under ice-cooling, and the mixture was stirred for 20 minutes. A solution (15 ml) of 5-acetoxy-2,3-dihydro-6,7-dimethoxy-2,4-dimethyl-2-benzofurancarbaldehyde (4.0 g) in tetrahydrofuran was added, and the mixture was stirred at room temperature for 30 minutes. The reaction mixture was poured into water, and the mixture was extracted with ethyl acetate. The extract was washed with saturated brine, dried over anhydrous magnesium sulfate and concentrated under reduced pressure. The residue was purified by column chromatography on silica gel (hexane:ethyl acetate=4:1) to obtain the title compound (3.1 g, 57%) as an oil.

$^1$H-NMR (CDCl$_3$) δ ppm: 1.29(3H,t,J=7.0 Hz), 1.60(3H, s), 1.97(3H,s), 2.33(3H,s), 3.00(1H,d,J=15.4 Hz), 3.11(1H, d, J=15.4 Hz), 3.84(3H,s), 3.94(3H,s), 4.20(2H,q,J=7.0 Hz), 5.85–5.95(1H,m), 6.07–6.49(2H,m), 7.20–7.33(1H,m).

Reference Example 11

Ethyl 5-(5-acetoxy-2,3-dihydro-6,7-dimethoxy-2,4-dimethylbenzofuran-2-yl)valerate 5% palladium-carbon (0.1 g) was added to a solution of ethyl 5-(5-acetoxy-2,3-dihydro-6,7-dimethoxy-2,4-dimethylbenzofuran-2-yl)pentadienoate (1.3 g) in ethanol (30 ml), and the mixture was stirred under an atmosphere of hydrogen at 50° C. for 5 hours. The reaction mixture was filtered, and the filtrate was concentrated under reduced pressure. The residue was purified by column chromatography on silica gel (hexane:ethyl acetate 7:3) to obtain the title compound (1.1 g, 86%) as an oil.

$^1$H-NMR (CDCl$_3$) δ ppm: 1.25(3H,t,J=6.8 Hz), 1.38–1.53 (2H,m), 1.43(3H,s), 1.60–1.82(4H,m), 1.96(3H,s), 2.28–2.35(2H,m), 2.32(3H,s), 2.79(1H,d,J=15.2 Hz), 2.95 (1H,d,J=15.2 Hz), 3.82(3H,s), 3.89(3H,s), 4.12(2H,q,J=6.8 Hz).

Reference Example 12

5-(2,3-Dihydro-5-hydroxy-6,7-dimethoxy-2,4-dimethylbenzofuran-2-yl)valeric acid

An aqueous 1N sodium hydroxide solution (30 ml) was added to a solution of ethyl 5-(5-acetoxy-2,3-dihydro-6,7-dimethoxy-2,4-dimethylbenzofuran-2-yl)valerate (2.3 g) in methanol (20 ml), and the mixture was stirred at room temperature for 2 hours. 1N hydrochloric acid was added to the reaction mixture, and the mixture was extracted with ethyl acetate. The extract was washed with saturated brine, dried over anhydrous magnesium sulfate and concentrated under reduced pressure to obtain the title compound (2.0 g, 96%) as an oil.

$^1$H-NMR (CDCl$_3$) δ ppm: 1.39–1.58(2H,m), 1.42(3H,s), 1.62–1.80(4H,m), 2.08(3H,s), 2.37(2H,t,J=7.4 Hz), 2.78 (1H,d,J=15.2 Hz), 2.94(1H,d,J=15.2 Hz), 3.90(6H,s), 5.40 (1H,br s).

Reference Example 13

4-[5-(2,3-dihydro-5-hydroxy-6,7-dimethoxy-2,4-dimethylbenzofuran-2-yl)pentanoyl]morpholine A solution (25 ml) of 5-(2,3-dihydro-5-hydroxy-6,7-dimethoxy-2,4-dimethylbenzofuran-2-yl)valeric acid (2.0 g), morpholine (0.81 ml) and 1-ethyl-3-(3-dimethylaminopropyl)-carbodiimide hydrochloride (1.4 g) in N,N-dimethylformamide was stirred under an atmosphere of argon at room temperature for 2 hours. The reaction mixture was made acidic by adding 1N hydrochloric acid to the mixture, and extracted with ethyl acetate. The extract was washed with saturated brine, dried over anhydrous magnesium sulfate and concentrated under reduced pressure. The residue was purified by column chromatography on silica gel (ethyl acetate) to obtain the title compound (2.1 g, 85%) as an oil.

$^1$H-NMR (CDCl$_3$) δ ppm: 1.39–1.55(2H,m), 1.60–1.80 (4H,m), 2.07(3H,s), 2.32(2H,t,J=7.2 Hz), 2.78(1H,d,J=15.0 Hz), 2.95(1H,d,J=15.0 Hz), 3.40–3.48(2H,m), 3.57–3.68 (6H,m), 3.90(6H,s), 5.37(1H,s).

Reference Example 14

4-[5-(2,3-dihydro-5-hydroxy-6,7-dimethoxy-2,4-dimethylbenzofuran-2-yl)pentyl]morpholine Lithium aluminum hydride (0.50 g) was added to a solution (30 ml) of 4-[5-(2,3-dihydro-5-hydroxy-6,7-dimethoxy-2,4-dimethylbenzofuran-2-yl)pentanoyl]morpholine (2.6 g) in tetrahydrofuran, and the mixture was stirred at room temperature for 30 minutes. The reaction mixture was poured into an aqueous sodium hydrosulfite solution, and the insoluble materials were filtered off. The filtrate was extracted with ethyl acetate. The extract was washed with saturated brine, dried over anhydrous sodium sulfate and concentrated under reduced pressure. The residue was purified by column chromatography on silica gel (ethyl acetate:methanol =95:5) to obtain the title compound (2.2 g, 88%) as an oil.

$^1$H-NMR (CDCl$_3$) δ ppm: 1.20–1.60(6H,m), 1.41(3H,s), 1.68–1.79(2H,m), 2.08(3H,s), 2.26–2.36(2H,m), 2.42(4H,t, J=4.8 Hz), 2.78(1H,d,J=15.2 Hz), 2.94(1H,d,J=15.2 Hz), 3.71(4H,t,J=4.8 Hz), 3.90(6H,s), 5.35(1H,br s).

Example 1

(S)-2-[2-Hydroxy-2-methyl-3-(4-phenylpiperidin-1-yl)propyl]-3,5,6-trimethyl-1,4-benzoquinone (A)

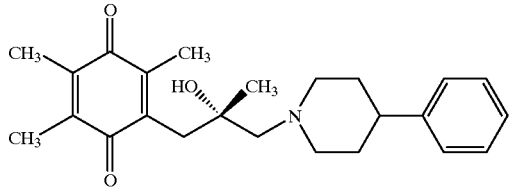

A suspension of Fremy salt (1.3 g) in distilled water (10 ml) was added to a solution of (S)-2,3-dihydro-2,4,6,7-tetramethyl-2-[(4-phenylpiperidin-1-yl)methyl]-5-benzofuran-5-amine (0.4 g) in ethanol (20 ml). The reaction mixture was stirred at room temperature for 30 minutes and diluted with water. The product was extracted with ethyl acetate. The extract was back-extracted with 1N hydrochloric acid. The aqueous layer was neutralized with a saturated aqueous solution of sodium bicarbonate, and the product was extracted with ethyl acetate. The extract was washed with water, dried over anhydrous magnesium sulfate and concentrated. The residue was dissolved in ethanol, and a hydrochloric acid—ethanol solution was added. The mixture was concentrated. The crude product thus obtained was recrystallized from ethanol to obtain the title compound (50 mg, 11%). mp. 180–190° C.

Elemental Analysis: Calcd. for $C_{24}H_{32}NO_3Cl.0.2H_2O$: C,68.38; H,7.75; N,3.32; Found: C,68.39; H,7.51; N,3.57

$^1$H-NMR (CDCl$_3$) of the free base, δ ppm: 1.19(3H,s), 1.60–1.90(4H,m), 2.04(6H,s), 2.11(3H,s), 2.30–2.60(3H,m), 2.41(2H,s), 2.64(1H,d,J=13.4 Hz), 2.88(1H,d,J=13.4 Hz), 2.90–3.15(2H,m), 3.44(1H,br s), 7.10–7.40(5H,m).

$[α]_D$=−36.4° (c=0.25, MeOH)

MS spectrum (FAB)(M: mass of the free base) 420 ([M+K]$^+$), 382([M+H]$^+$), 174(base peak).

Example 2

2-[2-Hydroxy-2-methyl-3-(4-phenylpiperidin-1-yl)propyl]-5,6-dimethoxy-3-methyl-1,4-benzoquinone hydrochloride

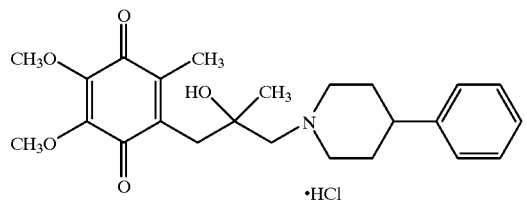

In the same manner as that described in Example 1, the title compound was obtained from 2,3-dihydro-6,7-dimethoxy-2,4-dimethyl-2-[(4-phenylpiperidin-1-yl)methyl]benzofuran-5-ol.

Yield: 24%. Amorphous.

$^1$H-NMR (DMSO-d$_6$) δ ppm: 1.59(3H,s), 1.80–2.10(2H, m), 1.99(3H,s), 2.23–2.49(3H,m), 2.70–3.70(6H,m), 3.78 (6H,br s), 3.80–4.00(2H,m), 7.15–7.40(5H,m), 10.22(1H,br s).

Example 3

2-(2-Hydroxy-2-methyl-7-morpholinoheptyl)-5,6-dimethoxy-3-methyl-1,4-benzoquinone hydrochloride

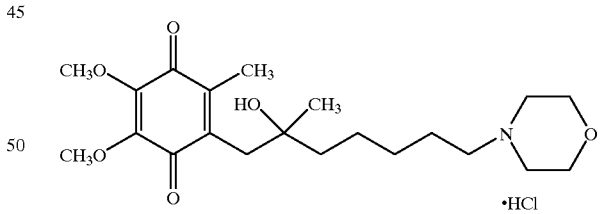

In the same manner as that described in Example 1, the title compound was obtained from 4-[5-(2,3-dihydro-5-hydroxy-6,7-dimethoxy-2,4-dimethylbenzofuran-2-yl)pentyl]morpholine.

Yield: 22%. Amorphous.

$^1$H-NMR (DMSO-d$_6$) δ ppm: 1.10–1.89(8H,m), 1.49(3H, s), 1.99(3H,s), 2.38–2.55(2H,m), 3.00(4H,br s), 3.35–3.90 (6H,m), 3.79(6H,br s), 11.00(1H,br s).

Preparation 1

The compound (A) was dissolved in physiological saline containing 30% (w/v) polyethylene glycol 400 to prepare a 0.05% solution of the compound (A). After sterilization with filtration, the solution was filled into vials (10 ml solution per vial). In this way, intravenously injectable preparations containing 5 mg of the compound per vial were produced.

As described above, the compound (I) or (I') of the present invention has lipoperoxide formation inhibitory effect and low toxicity. It is therefore useful as a medicine for treating or preventing central nervous system disorders, diseases in the circulatory system, inflammation, allergic diseases, etc.

We claim:

1. A compound of the formula:

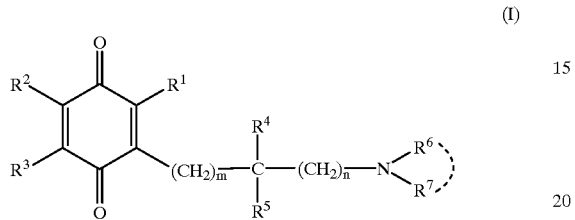

(I)

wherein $R^1$, $R^2$ and $R^3$ independently represent
  i) a hydrogen atom,
  ii) a hydroxyl group optionally substituted by a $C_{1-6}$ alkyl-carbonyl, $C_{6-10}$ aryl-carbonyl, $C_{6-10}$ aryl-$C_{1-6}$ alkyl-carbonyl, $C_{1-6}$ alkylsulfonyl, $C_{6-10}$ arylsulfonyl or $C_{6-10}$ aryl-$C_{1-6}$ alkylsulfonyl,
  iii) an amino group which may be substituted by 1 or 2 substituents selected from the group consisting of
    (a) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of $C_{1-3}$ alkyl, $C_{6-10}$ aryl-$C_{1-6}$ alkyl, $C_{6-10}$ aryl and 5- to 10-membered heteroaryl, and
    (b) a 5- to 10-membered heterocyclic group containing, besides carbon atoms, 1 to 3 hetero atoms selected from nitrogen atom, oxygen atom and sulfur atom, which group may be substituted by 1 to 5 substituents selected from the group consisting of amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto,
  iv) a $C_{1-6}$ alkoxy group optionally substituted by 1 to 5 substituents selected from the group consisting of amino, mono-$C_{1-3}$ alkylamino, di-$C_{1-3}$ alkylamino, halogen, hydroxyl, $C_{1-6}$ alkoxy and $C_{1-6}$ alkylmercapto, or
  v) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkynylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of $C_{1-3}$ alkyl, $C_{6-10}$ aryl-$C_{1-6}$ alkyl, $C_{6-10}$ aryl and 5- to 10-membered heteroaryl, or $R^2$ and $R^3$, taken together with the adjacent two carbon atoms, form a $C_{6-14}$ aromatic hydrocarbon or $C_{5-8}$ cycloalkene ring which may be substituted by 1 to 3 substituents selected from the group consisting of a $C_{1-3}$ alkyl, $C_{1-3}$ alkoxy, hydroxyl, halogen and amino;

$R^4$ represents a $C_{1-6}$ alkyl group;

$R^5$ represents a hydroxyl group optionally substituted by
  i) a $C_{1-6}$ alkyl, $C_{6-10}$ aryl, $C_{7-10}$ aralkyl, $C_{1-6}$ alkyl-carbonyl, $C_{6-10}$ aryl-carbonyl, $C_{7-10}$ aralkyl-carbonyl, tetrahydropyranyl or tetrahydrofuranyl group, each of which may be substituted by 1 to 3 substituents selected from the group consisting of halogen, $C_{1-6}$ alkyl, $C_{6-10}$ aryl, $C_{7-10}$ aralkyl and nitro, or
  ii) a formyl or silyl group, each of which may be substituted by 1 to 3 substituents selected from the group consisting of $C_{1-6}$ alkyl, $C_{6-10}$ aryl and $C_{7-10}$ aralkyl;

$R^6$ and $R^7$, taken together with the adjacent nitrogen atom, form a 3- to 7-membered N-containing heterocyclic ring optionally containing, besides carbon atoms and a nitrogen atom, 1 to 3 hetero atoms selected from nitrogen atom, oxygen atom and sulfur atom, which ring may be substituted by 1 to 5 substituents selected from the group consisting of amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl--carbonyl and $C_{1-3}$ alkylmercapto;

m represents 1 or 2; and n represents an integer of 1 to 5;

or a salt thereof.

2. A compound of the formula (I'):

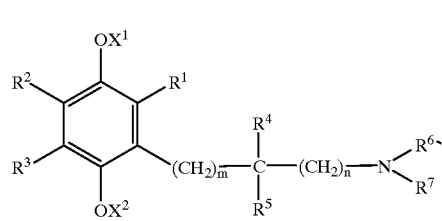

(I')

wherein $R_1$, $R^2$ and $R^3$ independently represent
  i) a hydrogen atom, ii) a hydroxyl group optionally substituted by a $C_{1-6}$ alkyl-carbonyl, $C_{6-10}$ aryl-carbonyl, $C_{6-10}$ aryl-$C_{1-6}$ alkyl-carbonyl, $C_{1-6}$ alkylsulfonyl, $C_{6-10}$ arylsulfonyl or $C_{6-10}$ aryl-$C_{1-6}$ alkylsulfonyl, iii) an amino group which may be substituted by 1 or 2 substituents selected from the group consisting of
   (a) $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of $C_{1-3}$ alkyl, $C_{6-10}$ aryl-$C_{1-6}$ alkyl, $C_{6-10}$ aryl and 5- to 10-membered heteroaryl, and (b) a 5- to 10-membered heterocyclic group containing, besides carbon atoms, 1 to 3 hetero atoms selected from nitrogen atom, oxygen atom and sulfur atom, which group may be substituted by 1 to 5 substituents selected from the group consisting of amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto, iv) a $C_{1-6}$ alkoxy group optionally substituted by 1 to 5 substituents selected from the group consisting of amino, mono-$C_{1-3}$ alkylamino, di-$C_{1-3}$ alkylamino, halogen, hydroxyl, $C_{1-6}$ alkoxy and $C_{1-6}$ alkylmercapto, or v) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkynylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of $C_{1-3}$ alkyl, $C_{6-10}$ aryl-$C_{1-6}$ alkyl, $C_{6-10}$ aryl and 5- to 10-membered heteroaryl, or $R^2$ and $R^3$, taken together with the adjacent two carbon atoms, form a $C_{6-14}$ aromatic hydrocarbon or $C_{5-8}$ cycloalkene ring which may be substituted by 1 to 3 substituents selected from the group consisting of a $C_{1-3}$ alkyl, $C_{1-3}$ alkoxy, hydroxyl, halogen and amino:

$R^4$ represents a $C_{1-6}$ alkyl group;

$R^5$ represents a hydroxyl group optionally substituted by
   i) a $C_{1-6}$ alkyl, $C_{6-10}$ aryl, $C_{7-10}$ aralkyl, $C_{1-6}$ alkyl-carbonyl, $C_{6-10}$ aryl-carbonyl, $C_{7-10}$ aralkyl-carbonyl, tetrahydropyranyl or tetrahydrofuranyl group, each of which may be substituted by 1 to 3 substituents selected from the group consisting of halogen, $C_{1-6}$ alkyl, $C_{6-10}$ aryl, $C_{7-10}$ aralkyl and nitro, or
   ii) a formyl or silyl group, each of which may be substituted by 1 to 3 substituents selected from the group consisting of $C_{1-6}$ alkyl, $C_{6-10}$ aryl and $C_{7-10}$ aralkyl;

$R^6$ and $R^7$, taken together with the adjacent nitrogen atom, form a 3- to 7-membered N-containing heterocyclic ring optionally containing, besides carbon atoms and a nitrogen atom, 1 to 3 hetero atoms selected from nitrogen atom, oxygen atom and sulfur atom, which ring maybe substituted by 1 to 5 substituents selected from the group consisting of amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto;

$X^1$ and $x^2$ independently represent
   i) a hydrogen atom,
   ii) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of $C_{1-3}$ alkyl, $C_{6-10}$ aryl-$C_{1-6}$ alkyl, $C_{6-10}$ aryl and 5- to 10-membered heteroaryl,
   iii) a $C_{6-14}$ aryl or a 5- to 11-membered heterocyclic group containing, besides carbon atoms, 1 to 4 hetero atoms selected from nitrogen atom, oxygen atom and sulfur atom, each of which group may be substituted by 1 to 5 substituents selected from the group consisting of an amino, mono-$C_{1-3}$ alkylamino, di-$C_{1-3}$ alkylamino, halogen, nitro, sulfo, cyano, hydroxyl, carboxyl, $C_{1-5}$ alkyl, $C_{6-14}$ aryl, $C_{1-3}$ alkoxy, $C_{1-4}$ alkyl-carbonyl and $C_{1-3}$ alkylmercapto, or
   iv) a $C_{2-6}$ alkanoyl group;

m represents 1 or 2; and n represents an integer of 1 to 5;

or a salt thereof.

3. A compound of claim 1, wherein $R^1$, $R^2$ and $R^3$ are independently a $C_{1-6}$ alkyl or $C_{1-6}$ alkoxy.

4. A compound of claim 1, wherein $R^4$ is a $C_{1-6}$ alkyl.

5. A compound of claim 1, wherein $R^5$ is hydroxyl.

6. A compound of claim 1, wherein $R^6$ and $R^7$, taken together with the adjacent nitrogen atom, form a 6-membered N-containing heterocyclic ring optionally containing, besides carbon atom(s) and a nitrogen atom, 1 to 3 hetero atoms selected from nitrogen atom, oxygen atom and sulfur atom, which ring may be substituted by a $C_{6-14}$ aryl.

7. A compound of claim 1, wherein $R^1$ is a $C_{1-6}$ alkyl, $R^2$ and $R^3$ are independently a $C_{1-6}$ alkyl or $C_{1-6}$ alkoxy, $R^4$ is a $C_{1-6}$ alkyl, $R^5$ is hydroxyl, $R^6$ and $R^7$, taken together with the adjacent nitrogen atom, form a 6-membered N-containing heterocyclic ring optionally containing, besides carbon atom(s) and a nitrogen atom, 1 to 3 hetero atoms selected from nitrogen atom and oxygen atom, which ring may be substituted by a $C_{6-14}$ aryl, m is 1, and n is 1 or 5.

8. A compound of claim 1, which is 2-[2-hydroxy-2-methyl-3-(4-phenylpiperidin-1-yl)propyl]-3,5,6-trimethyl-1,4-benzoquinone or a salt thereof.

9. A compound of claim 1, which is (S)-2-[2-hydroxy-2-methyl-3-(4-phenylpiperidin-1-yl)propyl]-3,5,6-trimethyl-1,4-benzoquinone or a salt thereof.

10. A pharmaceutical composition which comprises a pharmaceutically effective amount of a compound of claim 1 or claim 2 together with a pharmaceutically acceptable carrier.

11. A method of treating neurological disorders caused by central nervous system damage which comprises administering to a subject in need thereof a lipoperoxide formation inhibitory effective amount or a sodium channel blocking effective amount of a compound of claim 1 or claim 2, wherein the central nervous system damage is cranial injury or spinal injury.

12. A method of treating dysmnesia or emotional disturbance which comprises administering to a subject in need thereof a lipoperoxide formation inhibitory effective amount or a sodium channel blocking effective amount of a compound of claim 1 or claim 2.

13. A method of claim 12, wherein the dysmnesia or emotional disturbance is accompanied by nerve cell necrosis caused by cerebral lesion, cerebral hemorrhage or cerebral infarction.

14. A method for improving blood circulation in blood circulation disorders caused by damages to enzyme, tissue or cell of a living body due to active oxygen species comprising administering to a subject in need thereof a lipoperoxide formation inhibitory effective amount or a sodium channel blocking effective amount of a compound of claim 1 or claim 2.

15. The method of claim 14 wherein said enzyme, tissue or cell is in the brain or heart.

16. A method of claim 14, wherein said blood circulation disorder is ischemic disease.

17. A method for treating cerebral edema in a patient in need thereof comprising administering to said patient a lipoperoxide formation inhibitory effective amount or a sodium channel blocking effective amount of a compound of claim 1 or claim 2.

18. A process for producing a compound of claim 1 which comprises subjecting a compound of the formula (II):

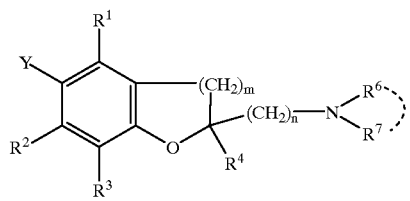

(II)

wherein Y represents —$NR^8R^9$ or —$OR^{10}$ wherein $R^8$, $R^9$ and $R^{10}$ independently represent
i) a hydrogen atom,
ii) a $C_{1-6}$ alkyl, $C_{2-6}$ alkenyl, $C_{2-6}$ alkynyl, $C_{3-6}$ cycloalkyl, $C_{6-14}$ aryl or $C_{6-10}$ aryl-$C_{1-6}$ alkyl group, each of which may be substituted by 1 to 5 substituents selected from the group consisting of a hydroxyl, $C_{1-3}$ alkoxy, $C_{6-10}$ aryl-$C_{1-6}$ alkoxy, $C_{6-10}$ aryloxy, 5- to 10-membered heteroaryloxy, mercapto, $C_{1-3}$ alkylthio, $C_{1-3}$ alkylsulfonyl, $C_{1-3}$ alkylsulfinyl, $C_{6-10}$ aryl-$C_{1-6}$ alkylthio, $C_{6-10}$ aryl-$C_{1-6}$ alkylsulfonyl, $C_{6-10}$ aryl-$C_{1-6}$ alkylsulfinyl, $C_{6-10}$ arylthio, 5- to 10-membered heteroarylthio, $C_{6-10}$ arylsulfonyl, 5- to 10-membered heteroarylsulfonyl, $C_{6-10}$ arylsulfinyl, 5- to 10-membered heteroarylsulfinyl, halogen, $C_{1-4}$ alkoxy-carbonyl, $C_{2-3}$ alkanoyl, $C_{2-3}$ alkanoyloxy, $C_{2-3}$ alkanoylamido, $C_{1-4}$ alkoxy-carbonylamino, 3- to 6-membered cyclic amino, carboxyl, carbamoyl and amino optionally substituted by 1 or 2 substituents selected from the group consisting of a $C_{1-3}$ alkyl, $C_{6-10}$ aryl-$C_{1-6}$ alkyl, $C_{6-10}$ aryl and 5- to 10-membered heteroaryl, or
iii) a $C_{2-6}$ alkanoyl group;
or a salt thereof,
to oxidation and if necessary subjecting the resultant compound to one or more of protection, reduction, acylation, alkylation, oxidation, hydrogenation, carbon-chain extension, substitution or deprotection.

* * * * *

UNITED STATES PATENT AND TRADEMARK OFFICE
CERTIFICATE OF CORRECTION

PATENT NO. : 6,011,046
DATED : January 4, 2000
INVENTOR(S) : Shigenori Ohkawa, et al.

It is certified that error appears in the above-identified patent and that said Letters Patent is hereby corrected as shown below:

Title page, item [56] References Cited,
OTHER PUBLICATIONS, "dicationary" should read -- Dictionary --; after "Diplock et al.", ""Vitamine E." should read -- "Vitamin E," --; and "healthe" should read -- health --.

Item [86],
PCT, "PCT No.: PCT/JP96/02313
    §371 Date: Oct. 26, 1996
    §102 (e) Date: Oct. 26, 1996" should read
-- PCT No.: PCT/JP96/02313
    §371 Date: Oct. 23, 1996
    §102 (e) Date: Oct. 23, 1996 --.

Column 1,
Line 46, "discloses" should read -- disclose --.

Column 2,
Line 26, "group or" should read -- group, or --;
Line 31, "(I)) or" should read -- (I)) ¶or --.

Column 3,
Line 52, "nitro ii)" should read -- nitro ¶ii) --.

Column 6,
Line 66, "substituent" should read -- substituents --.

Column 7,
Line 13, "substituent" should read -- substituents --;
Line 14, "substituent" should read -- substituents --;
Line 50, "phenetyloxy);" should read -- phenethyloxy); --.

Column 8,
Line 5, "heteroaylsulfinyl" should read -- heteroarylsulfinyl --;
Line 25, "substituent" (first occurrence) should read -- substituents --;
Line 41, "substituent" (first occurrence) should read -- substituents --.

UNITED STATES PATENT AND TRADEMARK OFFICE
CERTIFICATE OF CORRECTION

PATENT NO.    : 6,011,046
DATED         : January 4, 2000
INVENTOR(S)   : Shigenori Ohkawa, et al.

It is certified that error appears in the above-identified patent and that said Letters Patent is hereby corrected as shown below:

Column 10,
Line 41, "R" (first occurrence) should read -- $R^4$ --; "R" (second occurrence) should read -- $R^5$--, "R" (third occurrence) should read -- $R^6$ --; and "R" (fourth occurrence) should read -- $R^7$, --;
Line 57, "formula (A):" should read
-- formula (A):

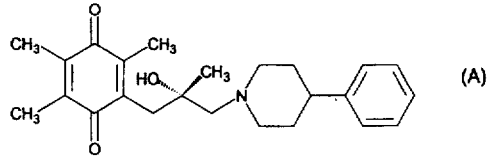

(A)

The salts of the compound (I) or (I') include salts used as synthetic intermediates and pharmaceutically acceptable salts. Examples of the salts include salts with inorganic bases, salts with organic bases, salts with inorganic acids, salts with organic acids, and salts with basic or acidic amino acids.
Preferred examples of the salts with inorganic bases include salts with alkaline metals such as sodium and potassium, salts with alkaline earth metals such as calcium and magnesium, aluminum salts, and ammonium salts. Preferred examples of the salts with organic bases include salts with trimethylamine, triethylamine, pyridine, picoline, 2,6-lutidine, ethanolamine, diethanolamine, triethylamine, cyclohexylamine, dicyclohexylamine and N,N'-dibenzylethylenediamine. Preferred examples of the salts with inorganic acids include salts with hydrochloric acid, hydrobromic acid, nitric acid, sulfuric acid and phosphoric acid. Preferred examples of the salts with organic acids include salts with formic acid, acetic acid, trifluoroacetic acid, phthalic acid, fumaric acid, oxalic acid, tartaric acid, --

Column 11,
Line 61, "includes," should read -- include, --

Column 12,
Lines 20 to 48 should be deleted;
Line 49, "acid," should be deleted.

Column 13,
Line 57, "nitrites" should read -- nitriles --.

UNITED STATES PATENT AND TRADEMARK OFFICE
CERTIFICATE OF CORRECTION

PATENT NO.   : 6,011,046
DATED        : January 4, 2000
INVENTOR(S)  : Shigenori Ohkawa, et al.

It is certified that error appears in the above-identified patent and that said Letters Patent is hereby corrected as shown below:

Column 14,
Line 20, "nitrites" should read -- nitriles --.

Column 15,
Line 49, "C1-6" should read -- $C_{1-6}$ --.

Column 16,
Line 5, "its thereof" should read -- its salt --;
Line 55, "Lou-Gehring's" should read -- Lou Gehrig's --.

Column 17,
Line 33, "include" should read -- includes --.

Column 18,
Line 17, ""%"" should read -- ¶"%" --;
Line 35, "Methods" should read -- ¶Methods --.

Column 19,
Line 21, "Na" should read -- $Na^+$ --;
Line 22, "0.9 M." should read -- 0.9 µM. --.

Column 26,
Line 28, "$C_{1-6}$" should read -- $C_{1-6}$ --;
Line 44, "maybe" should read -- may be --;
Line 66, "$R_1$," should read -- $R^1$, --.

Column 27,
Line 7, "$C_{1-6}$ alkyl," should read -- a $C_{1-6}$ alkyl, --;
Line 16, "heteroarylthlo," should read -- heteroarylthio, --;
Line 26, "and (b)" should read -- and ¶ (b) --.

Column 28,
Line 5, "alkyl- carbonyl," should read -- alkyl-carbonyl, --;
Line 20, "maybe" should read -- may be --;
Line 27, "$x^2$" should read -- $X^2$ --;
Line 66, "claim 1," should read -- claim 1 or 2, --.

UNITED STATES PATENT AND TRADEMARK OFFICE
CERTIFICATE OF CORRECTION

PATENT NO. : 6,011,046
DATED : January 4, 2000
INVENTOR(S) : Shigenori Ohkawa, et al.

It is certified that error appears in the above-identified patent and that said Letters Patent is hereby corrected as shown below:

Column 29,
Line 1, "claim 1," should read -- claim 1 or 2, --.
Line 2, "claim 1," should read -- claim 1 or 2, --.
Line 3, "claim 1," should read -- claim 1 or 2, --.
Line 10, "claim 1," should read -- claim 1 or 2, --.

Signed and Sealed this

Twenty-seventh Day of November, 2001

*Attest:*

*Attesting Officer*

NICHOLAS P. GODICI
*Acting Director of the United States Patent and Trademark Office*